United States Patent [19]

Weidmann et al.

[11] Patent Number: 5,726,305
[45] Date of Patent: Mar. 10, 1998

[54] SUBSTITUTED QUINOLINE-2-CARBOXAMIDES, THEIR PREPARATION AND THEIR USE AS PHARMACEUTICALS, AND INTERMEDIATES

[75] Inventors: Klaus Weidmann, Kronberg; Karl-Heinz Baringhaus, Wölfersheim; Georg Tschank, Klein-Winterheim; Martin Bickel, Bad Homburg, all of Germany

[73] Assignee: Hoechst Aktiengesellschaft, Frankfurt am Main, Germany

[21] Appl. No.: 675,155

[22] Filed: Jul. 3, 1996

[30] Foreign Application Priority Data

Sep. 28, 1995 [DE] Germany .................. 195 36 263.2
Feb. 13, 1996 [DE] Germany .................. 196 05 170.3

[51] Int. Cl.$^6$ .................. C07D 215/14; C07D 215/20
[52] U.S. Cl. .................. 546/156
[58] Field of Search .................. 546/156

[56] References Cited

U.S. PATENT DOCUMENTS 5,192,773  3/1993  Armistead et al. .............. 514/315
5,204,338  4/1993  Baader et al. .................. 514/183

FOREIGN PATENT DOCUMENTS 0 541 042  5/1993  European Pat. Off. .
0 562 512  9/1993  European Pat. Off. .
0 590 520  4/1994  European Pat. Off. .
0 650 960  5/1995  European Pat. Off. .
0 650 961  5/1995  European Pat. Off. .
0 661 269  7/1995  European Pat. Off. .

OTHER PUBLICATIONS

J. Am.Chem. Soc., Breslow et al., "Synthesis of Antimalarials. V. The Synthesis of Certain 4-Aminoquinoline Derivatives," vol. 68, (1946); pp 1232–1238.
Chem. Pharm. Bull., Kaneko et al., "The Isomerisation of 1aH-Oxazirino[2,3-a]quinoline 1a-carbonitrile . . . ," vol. 15, No. 5, (1967); pp. 663–669.
Gazz.Chim.Ital., Fattorusso et al., "Isolation of 3,4-dihydroxyquinoline2-carboxylic acid from the sponge Aplysina aerophoba," vol. 101, (1971); pp. 104–105.
J.Chem.Soc.C, Hannah, et al., "Removal of tolyl-sulphonyl groups from sulfonamides. III. some N-(tolyl-p-sulphonyl) glycine esters," No. 4, (1967); pp. 256–261.
J.Am.Chem.Soc., Boger et al., "(–) Sandramycin: Total Synthesis and Preliminary DNA Binding Properties," vol. 115, (1993); pp. 11624–11625.

J.Am.Chem.Soc., Konishi et al., "Structures of BBM-928 A,B, and C. Novel Antitumor Antibiotics from Actinomadura luzonensis," vol. 103, No. 5, (1981); pp. 1241–1243.
J.Chem.Soc.,Chem.Commum., Bayne et al., "Synthesis of 2-Acyl-3-hydroxyquinolines Embodying a Novel Variant of the Smiles Rearrangement," No. 19, (1975); pp. 782–783.
G. Jolles, et al., Bulletin de la Societe Chimique ee France, No. 8, 1965, pp. 2252–2259, with CAS RN 3458–69–3 attachment.
R.J. Bergeron, et al., Journal Of Medicinal Chemistry, vol. 37, No. 18, 1994, pp. 2889–2895.
T.J. Franklin, Biochem Soc. Trans., vol. 19(4), pp. 812–815, 1991.
G. Kaule et al., "Assay for 2-Oxoglutarate Decarboxylating Enzymes Based on the Determination of [1–14 C] Succinate: Application to Prolyl 4-Hydroxylase" Analytical Biochemistry, 184, pp. 291–297 (1990).
Kessler et al., "Syntheses des Benzylethers von Virginiamycin S1", Liebigs Annalen Der Chemie., Nr. 1, 1986, pp. 1–20.
J. Sheehan, "3-Hydroxypicolinic Acid and Some Of Its Derivatives, Journal of Organic Chemistry", vol. 31, Feb. 1996, pp. 636–638.
Chemical Abstracts, vol. 95, No. 17, 1981, Abstract No. 151135k with attachment: CAS RN 77431–62–0, CAS RN 77421–44–0 and CAS RN 77421–43–3.
Chemical Abstracts, vol. 12C, No. 324202v (1994).
Chemical Abstracts #107:130574 (Caplus #1987:530574), abstracts of J Antibiot, vol. 40(7), pp. 953–960, by Breiding-Mack, 1987.

Primary Examiner—C. Warren Ivy
Assistant Examiner—D. Margaret M. Mach
Attorney, Agent, or Firm—Finnegan, Henderson, Farabow, Garrett & Dunner, L.L.P.

[57] ABSTRACT

The invention relates to substituted quinoline-2-carboxylic acid amides of the formula I

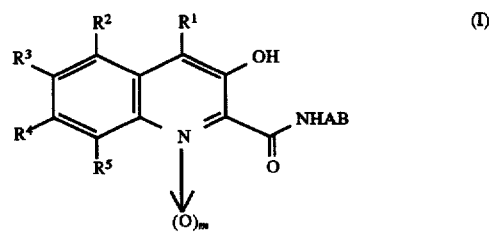

their preparation and their use, and intermediates which are formed in the preparation of the compounds of the formula I. The compounds according to the invention are used as inhibitors of prolyl 4-hydroxylase and as pharmaceuticals (medicaments) for treatment of fibrotic diseases.

1 Claim, No Drawings

SUBSTITUTED QUINOLINE-2-CARBOXAMIDES, THEIR PREPARATION AND THEIR USE AS PHARMACEUTICALS, AND INTERMEDIATES

The invention relates to substituted quinoline-2-carboxylic acid amides, to their preparation and their use as inhibitors of prolyl 4-hydroxylase, and to their use as pharmaceuticals for the treatment of fibrotic diseases, as well as to intermediates in their preparation.

Compounds which inhibit the enzymes prolyl and lysyl hydroxylase have the effect of very selective inhibition of collagen biosynthesis by influencing collagen-specific hydroxylation reactions. In the course thereof, protein-bound proline or lysine is hydroxylated by the enzymes prolyl or lysyl hydroxylase. If this reaction is suppressed by inhibitors, a nonfunctional hypohydroxylated collagen molecule which can be released by the cells into the extracellular space only in a small amount is formed. The hypohydroxylated collagen furthermore cannot be incorporated into the collagen matrix and is very readily degraded proteolytically. As a consequence of these effects, the amount of collagen deposited extracellularly is reduced overall.

Inhibitors of prolyl hydroxylase are therefore suitable substances in the treatment of diseases in which the deposition of collagens contributes decisively to the clinical picture. These include, inter alia, fibroses of the lung, liver and skin (scleroderma and scarring after burns, injuries and surgical operations) and atherosclerosis.

It is known that the enzyme prolyl hydroxylase is inhibited effectively by pyridine-2,4- and -2,5-dicarboxylic acid (K. Majamaa et al., Eur. J. Biochem. 138 (1984) 239–245). However, these compounds are active as inhibitors in the cell culture only at very high concentrations (Tschank, G et al., Biochem. J. 238 (1987) 625 to 633).

Prodrugs of pyridine-2,4(5)-dicarboxylates are also known. These are described in EP-A-0 590 520 and EP-A-0 562 512.

N-Oxalylglycines as inhibitors of prolyl 4-hydroxylase are known from J. Med. Chem. 1992, 35, 2652 to 2658 (Cunliffe et al.), and EP-A-0 457 163 Baader et al.).

3-Hydroxypyridine-2-carboxylic acid N-(carboxymethyl)amide is known from G. Yolles et al. in: Bull. Soc. Chim. Fr. 1965, 8, 2252 to 2259.

Hydroxyisoquinoline- and hydroxycinnolinecarboxylic acid glycylamides are known from Biochem. Soc. Trans. 1991, 19, 812 to 815 (Franklin et al.).

EP-A-0 661 269 describes substituted heterocyclic carboxylic acid amides and their use as inhibitors of prolyl 4-hydroxylase and as inhibitors of collagen biosynthesis.

The object was to search for even more active inhibitors of prolyl hydroxylase and for other inhibitors of collagen biosynthesis.

It has now been found that a selection of the compounds included in EP-A-0 661 269, that is to say the quinoline-2-carboxylic acid amides having an OH function in the ortho position relative to the amide function, show a surprisingly high inhibition of prolyl 4-hydroxylase in cell cultures.

The compounds according to the invention correspond to the formula (I)

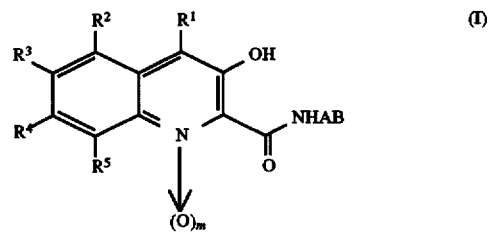

in which

A is $(C_1-C_4)$-alkylene, which is optionally substituted by one or two substituents from the series comprising halogen, cyano, nitro, trifluoromethyl, $(C_1-C_6)$-alkyl, $(C_1-C_6)$-hydroxyalkyl, $(C_1-C_6)$-alkoxy, —O—[$CH_2$]$_x$—$C_yH_{(2y+1-g)}$Hal$_g$, preferably $(C_1-C_8)$-fluoroalkoxy, $(C_1-C_8)$-fluoroalkenyloxy, $(C_1-C_8)$-fluoroalkynyloxy, —OCF$_2$Cl or —O—CF$_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, phenyl, benzyl, phenoxy, benzyloxy, anilino, N-methylanilino, phenylmercapto, phenylsulfonyl, phenylsulfinyl, sulfamoyl, N-$(C_1-C_4)$-alkylsulfamoyl and N,N-di-$(C_1-C_4)$-alkylsulfamoyl, or by a $(C_6-C_{12})$-aryloxy, $(C_7-C_{11})$-aralkyloxy, $(C_6-C_{12})$-aryl or $(C_7-C_{11})$-aralkyl radical, which carries, in the aryl part, 1, 2, 3, 4 or 5 identical or different substituents from the series comprising halogen, cyano, nitro, trifluoromethyl, $(C_1-C_6)$-alkyl, $(C_1-C_6)$-alkoxy, —O—[$CH_2$]$_x$—$C_yH_{(2y+1-g)}$Hal$_g$, —OCF$_2$Cl, —O—CF$_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, sulfamoyl, N-$(C_1-C_4)$-alkylsulfamoyl and N,N-di-$(C_1-C_4)$-alkylsulfamoyl, or by one or more substituents $R^*$ of the α-C atom of an α-amino acid, it being possible for the naturally occuring L-amino acids and their D isomers to be used;

B is an acid grouping from the series comprising —$CO_2H$, —CONHCOR"', —CONHSOR"', CONHSO$_2$R"', —NHSO$_2$CF$_3$, tetrazolyl, imidazolyl and 3-hydroxyisoxazolyl, in which R"' is aryl, heteroaryl, $(C_3-C_7)$-cycloalkyl or $(C_1-C_4)$-alkyl, optionally monosubstituted by $(C_6-C_{12})$-aryl, heteroaryl, OH, SH, $(C_1-C_4)$-alkyl, $(C_1-C_4)$-alkoxy, $(C_1-C_4)$-thioalkyl, -sulfinyl or -sulfonyl, CF$_3$, Cl, Br, F, I, NO$_2$, —COOH, $(C_2-C_5)$-alkoxycarbonyl, NH$_2$, mono- or di-$(C_1-C_4$-alkyl)-amino or $(C_1-C_4)$-perfluoroalkyl, $R^1$, $R^2$, $R^3$, $R^4$ and $R^5$ are identical or different and are hydrogen, hydroxyl, halogen, cyano, trifluoromethyl, nitro, carboxyl, $(C_1-C_{20})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_{12})$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, ($C_3$–$C_8$)-cycloalkoxy-($C_1$–$C_8$)-alkoxy-($C_1$–$C_8$)-alkoxy, ($C_6$–$C_{12}$)-aryl, ($C_7$–$C_{16}$)-aralkyl, ($C_7$–$C_{16}$)-aralkenyl, ($C_7$–$C_{16}$)-aralkynyl, ($C_2$–$C_{20}$)-alkenyl, ($C_2$–$C_{20}$)-alkynyl, ($C_1$–$C_{20}$)-alkoxy, ($C_2$–$C_{20}$)-alkenyloxy, ($C_2$–$C_{20}$)-alkynyloxy, retinyloxy, ($C_1$–$C_{20}$)-alkoxy-($C_1$–$C_{12}$)-alkyl, ($C_1$–$C_{12}$)-alkoxy-($C_1$–$C_{12}$)-alkoxy, ($C_1$–$C_{12}$)-alkoxy-($C_1$–$C_{12}$)-alkoxy-($C_1$–$C_8$)-alkyl, ($C_6$–$C_{12}$)-aryloxy, ($C_7$–$C_{16}$)-aralkyloxy, ($C_6$–$C_{12}$)-aryloxy-($C_1$–$C_6$)-alkoxy, ($C_7$–$C_{16}$)-aralkoxy-($C_1$–$C_6$)-alkoxy, ($C_1$–$C_{16}$)-hydroxyalkyl, ($C_6$–$C_{16}$)-aryloxy-($C_1$–$C_8$)-alkyl, ($C_7$–$C_{16}$)-aralkoxy-($C_1$–$C_8$)-alkyl, ($C_6$–$C_{12}$)-aryloxy-($C_1$–$C_8$)-alkoxy-($C_1$–$C_6$)-alkyl, ($C_7$–$C_{12}$)-aralkyloxy-($C_1$–$C_8$)-alkoxy-($C_1$–$C_6$)-alkyl, ($C_2$–$C_{20}$)-alkenyloxy-($C_1$–$C_8$)-alkyl, ($C_2$–$C_{20}$)-alkynyloxy-($C_1$–$C_8$)-alkyl, retinyloxy-($C_1$–$C_6$)-alkyl, —O—[$CH_2$—]$_x$$C_yH_{(2y+1-g)}$$F_g$, ($C_1$–$C_6$)-chlorofluoroalkoxy, such as —$OCF_2Cl$, —$OCF_2$—$CHFCl$, ($C_1$–$C_{20}$)-alkylcarbonyl, ($C_3$–$C_8$)-cycloalkylcarbonyl, ($C_6$–$C_{12}$)-arylcarbonyl, ($C_7$–$C_{16}$)-aralklcarbonyl, cinnamoyl, ($C_2$–$C_{20}$)-alkenylcarbonyl, ($C_2$–$C_{20}$)-alkynylcarbonyl, ($C_1$–$C_{20}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_2$–$C_{20}$)-alkenyloxycarbonyl, retinyloxycarbonyl, ($C_2$–$C_{20}$)-alkynyloxycarbonyl, ($C_6$–$C_{12}$)-aryloxy-($C_1$–$C_6$)-alkoxycarbonyl, ($C_7$–$C_{16}$)-aralkoxy-($C_1$–$C_6$)-alkoxycarbonyl, ($C_3$–$C_8$)-cycloalkyl-($C_1$–$C_6$)-alkoxycarbonyl, ($C_3$–$C_8$)-cycloalkoxy-($C_1$–$C_6$)-alkoxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_2$–$C_{12}$)-alkenylcarbonyloxy, ($C_2$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_2$–$C_{12}$)-alkenyloxycarbonyloxy, ($C_2$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N,N-dicyclo-($C_3$–$C_8$)-alkylcarbamoyl, N-($C_1$–$C_{10}$)-alkyl-N-($C_3$–$C_8$)-cycloalkylcarbamoyl, N-(($_3$–$C_8$)-cycloalkyl-($C_1$–$C_6$)-alkyl)carbamoyl, N-($C_1$–$C_6$)-alkyl-N-(($C_3$–$C_8$)-cycloalkyl-($C_1$–$C_6$)-alkyl)carbamoyl, N-(+)-dehydroabietylcarbamoyl, N-($C_1$–$C_6$)-alkyl-N-(+)-dehydroabietylcarbamoyl, N-($C_6$–$C_{12}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{12}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$) carbamoyl, N-($C_1$–$C_{10}$)-alkyl-N-(($C_6$–$C_{12}$)-aryloxy-($C_1$–$C_{10}$)-alkyl)carbamoyl, N-($C_1$–$C_{10}$)-alkyl-N-($C_7$–$C_{16}$)-aralkyloxy-($C_1$–$C_{10}$)-alkyl)carbamoyl, CON ($CH_2$)$_h$, in which a $CH_2$ group can be replaced by O, S, N-($C_1$–$C_{12}$)-alkylimino, N-($C_3$–$C_8$)-cycloalkylimino, N-($C_3$–$C_8$)-cycloalkyl-($C_1$–$C_{12}$)-alkylimino, N-($C_6$–$C_{12}$)-arylimino, N-($C_7$–$C_{16}$)-aralkylimino or N-($C_1$–$C_{12}$)-alkoxy-($C_1$–$C_6$)-alkylimino and h is 3 to 7, or a carbamoyl radical of the formula J

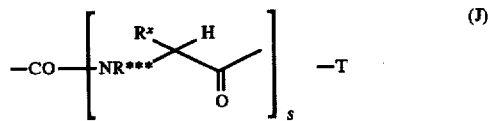

in which

R* is the substituent of an α-amino acid, which includes the L- and D-amino acids, s is 1, 2, 3, 4 or 5 and T is OH, OR or NR*R**, in which R*, R and R* are identical or different and are hydrogen, ($C_6$–$C_{12}$)-aryl, ($C_7$–$C_{11}$)-aralkyl, ($C_1$–$C_8$)-alkyl, ($C_3$–$C_8$)-cycloalkyl, (+)-dehydroabietyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkylcarbonyl, optionally substituted ($C_7$–$C_{16}$)-aralkylcarbonyl or optionally substituted ($C_6$–$C_{12}$)-arylcarbonyl, or R* and R** together are —[$CH_2$]$_h$, in which one $CH_2$ group can be replaced by O, S, SO, $SO_2$, N-acylamino, N-($C_1$–$C_{10}$)-alkoxycarbonylimino, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-aralkylimino, N-($C_7$–$C_{16}$)-aralkylimino or N-($C_1$–$C_4$)-alkoxy-($C_1$–$C_6$)-alkylimino and h is 3 to 7, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{12}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkyl)carbamoyloxy, N-(($C_6$–$C_{12}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy)-($C_1$–$C_{10}$)-alkyl)carbamoyloxy, N-($C_1$–$C_{10}$)-alkyl-N-(($C_6$–$C_{12}$)-aryloxy)-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-alkyl-aralkylamino, N-alkyl-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkylcarbonylamino, ($C_3$–$C_8$)-cycloalkylcarbonylamino, ($C_6$–$C_{12}$)-arylcarbonylamino, ($C_7$–$C_{16}$)-aralkylcarbonylamino, ($C_1$–$C_{12}$)-alkylcarbonyl-N-($C_1$–$C_{10}$)-alkylamino, ($C_3$–$C_8$)-cycloalkylcarbonyl-N-($C_1$–$C_{10}$)-alkylamino, ($C_6$–$C_{12}$)-arylcarbonyl-N-($C_1$–$C_{10}$)-alkylamino, ($C_7$–$C_{11}$)-aralkylcarbonyl-N-($C_1$–$C_{10}$)-alkylamino, ($C_1$–$C_{12}$)-alkylcarbonylamino-($C_1$–$C_8$)-alkyl, ($C_3$–$C_8$)-cyclo-alkylcaarbonylamino-($C_1$–$C_8$)-alkyl, ($C_6$–$C_{12}$)-arylcarbonylamino-($C_1$–$C_8$)-alkyl, ($C_7$–$C_{16}$)-aralkylcarbonylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{20}$)-alkylmercapto, ($C_1$–$C_{20}$)-alkyl-sulfinyl, ($C_1$–$C_{20}$)-alkylsulfonyl, ($C_6$–$C_{12}$)-arylmercapto, ($C_6$–$C_{12}$)-arylsulfinyl, ($C_6$–$C_{12}$)-arylsulfonyl, ($C_7$–$C_{16}$)- aralkylmercapto, $(C_7-C_{16})$-aralkylsulfinyl, $(C_7-C_{16})$-aralkylsulfonyl, $(C_1-C_{12})$-alkylmercapto-$(C_1-C_6)$-alkyl, $(C_1-C_{12})$-alkylsulfinyl-$(C_1-C_6)$-alkyl, $(C_1-C_{12})$-alkylsulfonyl-$(C_1-C_6)$-alkyl, $(C_6-C_{12})$-arylmercapto-$(C_1-C_6)$-alkyl, $(C_6-C_{12})$-arylsulfinyl-$(C_1-C_6)$-alkyl, $(C_6-C_{12})$-arylsulfonyl-$(C_1-C_6)$-alkyl, $(C_7-C_{16})$-aralkylmercapto-$(C_1-C_6)$-alkyl, $(C_7-C_{16})$-aralkylsulfinyl-$(C_1-C_6)$-alkyl, $(C_7-C_{16})$-aralkylsulfonyl-$(C_1-C_6)$-alkyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{12})$-arylsulfamoyl, N-$(C_7-C_{16})$-aralkylsulfamoyl, N-$(C_1-C_{10})$-alkyl-N-$(C_6-C_{12})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$-alkyl$)$-$(C_1-C_{10})$-alkylsulfonamido, $(C_7-C_{16})$-aralkylsulfonamido, or N-$(C_1-C_{10})$-alkyl-$(C_7-C_{16})$-aralkylsulfonamido, where the radicals which contain an aryl radical can in turn be substituted on the aryl by 1 to 5 identical or different radicals from the series comprising:

hydroxyl, halogen, cyano, trifluoromethyl, nitro, carboxyl, $(C_1-C_{16})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cyclo-alkyloxy-$(C_1-C_8)$-alkoxy-$(C_1-C_6)$-alkyl, $(C_3-C_8)$-cyclo-alkoxy-$(C_1-C_8)$-alkoxy-$(C_1-C_8)$-alkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, —O—$[CH_2]_xC_yH_{(2y+1-g)}F_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-$((C_3-C_8)$-cycloalkyl-$(C_1-C_6)$-alkyl$)$carbamoyl, N-$(C_1-C_6)$-alkyl-N-$((C_3-C_8)$-cycloalkyl-$(C_1-C_6)$-alkyl$)$carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{16})$-alkoxy-$(C_1-C_{10})$-alkyl$)$carbamoyl, N-$((C_6-C_{16})$-aryloxy-$(C_1-C_{10})$-alkyl$)$carbamoyl, N-$((C_7-C_{16})$-aralkyloxy-$(C_1-C_{10})$-alkyl$)$carbamoyl, N-$(C_1-C_{10})$-alkyl-N-$((C_1-C_{10})$-alkoxy-$(C_1-C_{10})$-alkyl$)$carbamoyl, N-$(C_1-C_{10})$-alkyl-N-$((C_6-C_{12})$-aryloxy-$(C_1-C_{10})$-alkyl$)$carbamoyl, N-$(C_1-C_{10})$-alkyl-N-$((C_7-C_{16})$-aralkyloxy-$(C_1-C_{10})$-alkyl$)$carbamoyl, CON$(CH_2)_h$, in which one CH$_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino and h is 3 to 7, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkyl$)$carbamoyloxy, N-$((C_6-C_{12})$-aryloxy-$(C_1-C_{10})$-alkyl$)$carbamoyloxy, N-$((C_7-C_{16})$-aralkyloxy-$(C_1-C_{10})$-alkyl$)$carbamoyloxy, N-$(C_1-C_{10})$-alkyl-N-$((C_1-C_{10})$-alkoxy-$(C_1-C_{10})$-alkyl$)$carbamoyloxy, N-$(C_1-C_{10})$-alkyl-N-$((C_6-C_{12})$-aryloxy-$(C_1-C_{10})$-alkyl$)$carbamoyloxy, N-$(C_1-C_{10})$-alkyl-N-$((C_7-C_{16})$-aralkyloxy-$(C_1-C_{10})$-alkyl$)$carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkylcarbonylamino, $(C_3-C_8)$-cycloalkylcarbonylamino, $(C_6-C_{12})$-arylcarbonylamino, $(C_7-C_{16})$-aralkylcarbonylamino, $(C_1-C_{12})$-alkylcarbonyl-N-$(C_1-C_{10})$-alkylamino, $(C_3-C_8)$-cycloalkylcarbonyl-N-$(C_1-C_{10})$-alkylamino, $(C_6-C_{12})$-arylcarbonyl-N-$(C_1-C_{10})$-alkylamino, $(C_7-C_{11})$-aralkylcarbonyl-N-$(C_1-C_{10})$-alkylamino, $(C_1-C_{12})$-alkylcarbonylamino-$(C_1-C_8)$-alkyl, $(C_3-C_8)$-cycloalkylcarbonylamino-$(C_1-C_8)$-alkyl, $(C_6-C_{12})$-arylcarbonylamino-$(C_1-C_8)$-alkyl, $(C_7-C_{16})$-aralkylcarbonylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, ($C_1$–$C_{12}$)-alkylmercapto, ($C_1$–$C_{12}$)-alkylsufinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-araylkylmercapto, ($C_7$–$C_{16}$)-aralkylsulfinyl and ($C_7$–$C_{16}$)-aralkylsulfonyl, or R and $R^2$, $R^2$ and $R^3$, $R^3$ and $R^4$, or $R^4$ and $R^5$ form a chain $[CH_2]_o$, in which one or two $CH_2$ groups of the chain, which is saturated or unsaturated with a C=C double bond, are optionally replaced by O, S, SO, $SO_2$ or NR', in which o is 3, 4 or 5, and R' is hydrogen, ($C_6$–$C_{12}$)-aryl, ($C_1$–$C_8$)-alkyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkylcarbonyl, optionally substituted ($C_7$–$C_{16}$)-aralkylcarbonyl or optionally substituted ($C_6$–$C_{12}$)-arylcarbonyl, and m is 0 or 1, f is 1 to 8, g is 0 or 1 to (2f+1), x is 0 to 3 and h is 3 to 6, including the physiologically active salts.

Aryl is understood as meaning, in particular, phenyl and naphthyl which are unsubstituted or preferably substituted as described, heteroaryl is understood as meaning, in particular, pyridyl, picolyl or thienylmethyl which are unsubstituted or substituted as described, cycloakyl is preferably understood as meaning cyclohexyl and halogen is understood as meaning, in particular, fluorine, chlorine and bromine.

The invention furthermore relates to salts of the compounds of the formula I. The salt formation with basic reagents can take place on one or two acid groups of the compounds of the formula I, i.e. on the radicals B, $R^1$, $R^2$, $R^3$, $R^4$ and $R^5$ and/or on the acid phenolic OH group, in particular on the radicals B and the phenolic OH group.

Reagents which are used are, for example, alcoholates, hydroxides, carbonates, bicarbonates, hydrogen phosphates and/or metal-organyls of the alkali metal and alkaline earth metal elements, the elements of main groups 3 and 4 of the periodic table and the elements of the transition metals, amines, optionally mono- to trisubstituted by ($C_1$–$C_8$)-hydroxyalkyl, ($C_1$–$C_4$)-alkoxy-($C_1$–$C_8$)-alkyl, phenyl, benzyl or ($C_1$–$C_8$)-alkyl, which can be mono- to trisubstituted by hydroxyalkyl, hydroxyl or ($C_1$–$C_4$)-alkoxy, for example Tromethane (Tris buffer), 2-aminoethanol, 3-aminopropanol, hydroxylamine, dimethylhydroxylamine, 2-methoxy-ethylamine and 3-ethoxypropylamine, and basic amino acids and derivatives, such as amino acid esters, histidine, arginine and lysine and derivatives thereof, and medicaments which contain a basic group, such as, for example, amiloride, verapamil and beta-blockers.

The invention furthermore relates to the compounds according to the formula I for use as medicaments.

Compounds of the formula I which are of particular importance are those in which:

A is ($C_1$–$C_3$)-alkylene, which is optionally mono-substituted by halogen, cyano, trifluoromethyl, ($C_1$–$C_6$)-alkyl, ($C_1$–$C_6$)-hydroxyalkyl, ($C_1$–$C_6$)-alkoxy or —O—$[CH_2]_x$—$C_fH_{(2f+1-g)}F_g$ or A is —$CHR^x$—, in which $R^x$ is one of the substituents of the αC atom of an α-amino acid, in particular of a naturally occuring L-amino acid or its D isomer, B is —$CO_2H$, $R^1$ and $R^5$ are identical or different and are hydrogen, ($C_1$–$C_{12}$)-alkyl, ($C_2$–$C_{12}$)-alkenyl, chlorine, fluorine, bromine, trifluoromethyl, ($C_1$–$C_{12}$)-alkylsulfonyl, ($C_1$–$C_{12}$)-alkylsulfinyl, ($C_1$–$C_{10}$)-alkoxy, —O—$[CH_2]_x$—$C_fH_{(2f+1-g)}F_g$, ($C_1$–$C_6$)-alkoxy-($C_1$–$C_6$)-alkoxy or ($C_3$–$C_8$)-cycloalkoxy, phenylsulfonyl or phenylsulfinyl, where phenyl is optionally substituted by fluorine, chlorine or ($C_1$–$C_5$)-alkoxy;

$R^2$, $R^3$ and $R^4$ are identical or different and are hydrogen, hydroxyl, ($C_1$–$C_{20}$)-alkyl, ($C_2$–$C_{20}$)-alkenyl, ($C_2$–$C_{20}$)-alkynyl, ($C_1$–$C_{20}$)-alkoxy, ($C_2$–$C_{20}$)-alkenyloxy, ($C_2$–$C_{20}$)-alkynyloxy, retinyloxy, ($C_1$–$C_{20}$)-alkoxy-($C_1$–$C_8$)-alkyl, ($C_2$–$C_{20}$)-alkenyloxy-($C_1$–$C_8$)-alkyl, retinyloxy-($C_1$–$C_6$)-alkyl, ($C_2$–$C_{20}$)-alkynyloxy-($C_1$–$C_8$)-alkyl, halogen, cyano, trifluoromethyl, ($C_1$–$C_{12}$)-hydroxyalkyl, ($C_1$–$C_{20}$)-alkylcarbonyl, ($C_7$–$C_{16}$)-aralkylcarbonyl, ($C_6$–$C_{12}$)-arylcarbonyl, ($C_6$–$C_{12}$)-aryl, ($C_7$–$C_{16}$)-aralkyl, —O—$[CH_2]_x$—$C_fH_{(2f+1-g)}F_g$, ($C_1$–$C_{18}$)-alkylmercapto, ($C_1$–$C_{18}$)-alkylsulfinyl, ($C_1$–$C_{18}$)-alkylsulfonyl, ($C_6$–$C_{12}$)-arylmercapto, ($C_6$–$C_{12}$)-arylsulfinyl), ($C_6$–$C_{12}$)-arylsulfonyl, ($C_7$–$C_{12}$)-aralkylmercapto, ($C_7$–$C_{12}$)-aralkylsulfinyl, ($C_7$–$C_{12}$)-aralkylsulfonyl, ($C_6$–$C_{12}$)-aryloxy, ($C_7$–$C_{16}$)-aralkyloxy, carboxyl, ($C_1$–$C_{20}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_2$–$C_{20}$)-alkenyloxycarbonyl, retinyloxycarbonyl, ($C_2$–$C_{20}$)-alkynyloxycarbonyl, ($C_3$–$C_8$)-cycloalkyl-($C_1$–$C_6$)-alkoxycarbonyl, ($C_3$–$C_8$)-cycloalkoxy-($C_1$–$C_6$)-alkoxycarbonyl, ($C_6$–$C_{12}$)-aryloxy-($C_1$–$C_6$)-alkoxycarbonyl, ($C_7$–$C_{16}$)-aralkoxy-($C_1$–$C_6$)-alkoxycarbonyl, —O—$[CH_2]_x$—$C_fH_{(2f+1-g)}Hal_g$, ($C_1$–$C_{12}$)-alkyl, ($C_1$–$C_{12}$)-alkoxy-($C_1$–$C_{12}$)-alkoxy, ($C_1$–$C_{12}$)-alkoxy-($C_1$–$C_{12}$)-alkoxy-($C_1$–$C_6$)-alkyl, ($C_7$–$C_{11}$)-aralkyloxy, ($C_3$–$C_8$)-cycloalkyl, ($C_3$–$C_8$)-cycloalkyl-($C_1$–$C_{12}$)-alkyl, ($C_3$–$C_8$)-cycloalkyloxy, ($C_3$–$C_8$)-cycloalkyl-($C_1$–$C_8$)-alkoxy, ($C_3$–$C_8$)-cycloalkyloxy-($C_1$–$C_{12}$)-alkyl, ($C_3$–$C_8$)-cycloalkyloxy-($C_1$–$C_8$)-alkoxy, ($C_3$–$C_8$)-cycloalkyl-($C_1$–$C_{12}$)-alkyl-($C_1$–$C_6$)-alkoxy, ($C_3$–$C_8$)-cycloalkyl-($C_1$–$C_6$)-alkoxy-($C_1$–$C_6$)-alkyl, ($C_3$–$C_8$)-cycloalkoxy-($C_1$–$C_6$)-alkoxy-($C_1$–$C_6$)-alkyl, $NR^YR^Z$, substituted ($C_6$–$C_{12}$)-aryloxy-($C_1$–$C_6$)-alkyl, ($C_7$–$C_{11}$)-aralkoxy-($C_1$–$C_6$)-alkyl, ($C_6$–$C_{12}$)-aryloxy-($C_1$–$C_6$)-alkoxy-($C_1$–$C_6$)-alkyl, ($C_7$–$C_{11}$)-aralkyloxy-($C_1$–$C_6$)-alkoxy-($C_1$–$C_6$)-alkyl, ($C_6$–$C_{12}$)-aryloxy-($C_1$–$C_6$)-alkoxy or ($C_7$–$C_{11}$)-aralkoxy-($C_1$–$C_6$)-alkoxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N,N-dicyclo($C_3$–$C_8$)-alkylcarbamoyl, N-($C_1$–$C_{10}$)-alkyl-N-($C_3$–$C_8$)-cycloalkylcarbamoyl, N-($C_3$–$C_8$)-cycloalkyl-($C_1$–$C_{16}$)-alkyl)carbamoyl, N-($C_1$–$C_6$)-alkyl-N-(($C_3$–$C_8$)-cycloalkyl-($C_1$–$C_6$)-alkyl)carbamoyl, N-(+)-dehydroabietylcarbamoyl, N-($C_1$–$C_6$)-alkyl-N-(+)-dehydroabietylcarbamoyl, N-($C_6$–$C_{12}$)-arylcarbamoyl, N-($C_7$–$C_{16}$)-aralkyl-carbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{12}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_6$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{12}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, or $CON(CH_2)_h$, in which one $CH_2$ group can be replaced by O, S, N-($C_1$-$C_{16}$)-alkylimino, N-($C_3$-$C_8$)-cycloalkylimino, N-($C_3$-$C_8$)-cycloalkyl-($C_1$-$C_{12}$)-alkylimino, N-($C_6$-$C_{12}$)-arylimino, N-($C_7$-$C_{16}$)-aralkylimino or N-($C_1$-$C_{12}$)-alkoxy-($C_1$-$C_6$)-alkylimino and h is 3 to 7, where an aromatic radical carries 1, 2, 3, 4 or 5 identical or different substituents from the series comprising halogen, cyano, nitro, hydroxyl, trifluoromethyl, ($C_1$-$C_{16}$)-alkyl, ($C_2$-$C_{16}$)-alkenyl, ($C_1$-$C_6$)-hydroxyalkyl, ($C_1$-$C_{16}$)-alkoxy, ($C_1$-$C_{16}$)-alkenyloxy, —O—[$CH_2$]$_x$—$C_fH_{(2f+1-g)}F_g$, —$OCF_2Cl$, —O—$CF_2$—$CHFCl$, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N-($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkylcarbamoyl, phenyl, benzyl, phenoxy, benzyloxy, phenylmercapto, phenylsulfonyl, phenylsulfinyl, sulfamoyl, N-($C_1$-$C_4$)-alkylsulfamoyl and N,N-di-($C_1$-$C_4$)-alkylsulfamoyl, or optionally carries up to 3 of the abovementioned identical or different substituents and two adjacent carbon atoms of the aralkyloxy radical together carry a chain —[$CH_2$]— and/or —CH=CH—CH=CH—, where one $CH_2$ group of the chain is optionally replaced by O, S, SO, $SO_2$ or NR', $R^Y$ and $R^Z$ are identical or different and are hydrogen, ($C_6$-$C_{12}$)-aryl, ($C_1$-$C_{10}$)-alkyl, ($C_3$-$C_{10}$)-cycloalkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, or optionally substituted ($C_6$-$C_{12}$)-aroyl, or $R^Y$ and $R^Z$ together are —[$CH_2$]$_h$—, wherein one CH group can be replaced by O, S, N—($C_1$-$C_4$)-alkanoylimino or N—($C_1$-$C_4$)-alkoxycarbonylimino, m is 0 or 1, f is 1 to 8, g is 0 or 1 to (2f+1), h is 3 to 6 and x is 0 to 3, including the physiologically active salts.

Particularly preferred compounds of the formula I are those in which m is 0,

A is a —$CH_2$— group, which can be substituted by a methyl group,

B is —$CO_2H$, $R^1$ is hydrogen, ($C_1$-$C_4$)-alkyl, ($C_1$-$C_4$)-alkoxy, chlorine or bromine, $R^5$ is hydrogen, fluorine, chlorine or methyl and $R^2$, $R^3$ and $R^4$ are identical or different and are hydrogen, ($C_1$-$C_{18}$)-alkyl, ($C_2$-$C_{18}$)-alkenyl, ($C_2$-$C_{18}$)-alkynyl, phenyl, chlorine, fluorine, bromine, hydroxyl, trifluoromethyl, ($C_1$-$C_{18}$)-alkylsulfinyl, ($C_1$-$C_{18}$)-alkylsulfonyl, phenylsulfinyl, phenylsulfonyl, naphthylsulfinyl, naphthylsulfonyl, ($C_1$-$C_{18}$)-alkoxy, ($C_3$-$C_8$)-cycloalkoxy, ($C_1$-$C_8$)-alkoxy-($C_1$-$C_8$)-alkoxy, —O—[$CH_2$]$_x$—$C_fH_{(2f+1-g)}F_g$, phenyl-($C_1$-$C_4$)-alkoxy, phenoxy, ($C_1$-$C_{12}$)-alkanoyl, phenyl-($C_1$-$C_4$)-alkanoyl or benzoyl, where, in substituents with a phenyl or naphthyl ring, this optionally carries up to 5 identical or different substituents from the series comprising fluorine, chlorine, bromine, nitrile, trifluoromethyl, $C_1$-$C_6$)-alkyl, ($C_1$-$C_6$)-alkoxy, —O—[$CH_2$]$_x$—$C_fH_{((2f+1-g)}F_g$ or ($C_1$-$C_6$)-alkylsulfonyl, including the physiologically active salts.

Especially preferred compounds of the formula I are those in which m is 0,

A is a —$CH_2$— group,

B is —$CO_2H$, $R^1$ and $R^5$ are hydrogen and $R^2$, $R^3$ and $R^4$ are identical or different and are hydrogen, ($C_1$-$C_{18}$)-alkyl, ($C_2$-$C_{18}$)-alkenyl, phenyl, chlorine, fluorine, bromine, trifluoromethyl, ($C_1$-$C_{18}$)-alkylsulfinyl, ($C_1$-$C_{18}$)-alkylsulfonyl, phenylsulfinyl, phenylsulfonyl, naphthylsulfinyl, naphthylsulfonyl, ($C_1$-$C_{18}$)-alkoxy, ($C_3$-$C_8$)-cycloalkoxy, ($C_1$-$C_8$)-alkoxy-($C_1$-$C_8$)-alkoxy, —O—[$CH_2$]$_x$—$C_fH_{(2f+1-g)}F_g$, phenyl-($C_1$-$C_4$)-alkoxy, phenoxy, ($C_1$-$C_{12}$)-alkylcarbonyl, phenyl-($C_1$-$C_4$)-alkylcarbonyl or benzylcarbonyl, where, in substituents having a phenyl or naphthyl ring, this optionally carries up to 5 identical or different substituents from the series comprising fluorine, chlorine, bromine, nitrile, trifluoromethyl, ($C_1$-$C_6$)-alkyl, ($C_1$-$C_6$)-alkoxy, —O—[$CH_2$]$_x$—$C_fH_{(2f+1-g)}F_g$ and ($C_1$-$C_6$)-alkylsulfonyl, including the physiologically active salts.

Particularly preferred compounds of the formula I are those in which m is 0,

A is a —$CH_2$— group, $R^1$ and $R^5$ are hydrogen, one of the substituents $R^2$, $R^3$ or $R^4$ is hydrogen and the other two are identical or different and are hydrogen, ($C_1$-$C_{16}$)-alkyl, fluorine, chlorine, bromine, trifluoromethyl, ($C_1$-$C_{16}$)-alkylsulfonyl, phenylsulfonyl, ($C_1$-$C_{16}$)-alkoxy, ($C_1$-$C_8$)-alkoxy-($C_1$-$C_8$)-alkoxy, —O—[$CH_2$]$_x$—$C_fH_{(2f+1g)}F_g$, benzyloxy or phenoxy, where, in substituents which contain a phenyl ring, this optionally carries up to 3 substituents from the series comprising fluorine, chlorine, bromine, trifluoromethyl, ($C_1$-$C_6$)-alkyl, ($C_1$-$C_6$)-alkoxy, —O—[$CH_2$]$_x$— $C_fH_{(2f+1-g)}F_g$ or ($C_1$-$C_4$)-alkylsulfonyl, including the physiologically active salts.

Particularly preferred compounds of the formula I are those in which m is 0,

A is a —$CH_2$— group, $R^1$, $R^2$ and $R^5$ are hydrogen and $R^3$ and $R^4$ are identical or different and are hydrogen, ($C_1$-$C_{16}$)-alkyl, fluorine, chlorine, trifluoromethyl, ($C_1$-$C_{16}$)-alkylsulfonyl, phenylsulfonyl, naphthylsulfonyl, ($C_1$-$C_{16}$)-alkoxy, ($C_1$-$C_8$)-alkoxy-($C_1$-$C_8$)-alkoxy, —O—[$CH_2$]$_x$—$C_fH_{(2f+1-g)}F_g$, benzyloxy or phenoxy, where, in substituents which contain a phenyl ring, this optionally carries up to 3 substituents from the series comprising fluorine, chlorine, trifluoromethyl, ($C_1$-$C_6$)-alkyl, ($C_1$-$C_6$)-alkoxy, —O—[$CH_2$]$_x$—$C_fH_{(2f+1-g)}F_g$ and ($C_1$-$C_4$)-alkylsulfonyl, including the physiologically active salts.

Particularly preferred compounds of the formula I are furthermore those in which m is 0, A is a —$CH_2$— group, $R^1$, $R^2$, $R^3$ and $R^5$ are hydrogen and $R^4$ is hydrogen, ($C_1$-$C_{12}$)-alkyl, fluorine, chlorine, bromine, trifluoromethyl, ($C_1$-$C_{12}$)-alkylsulfonyl, phenylsulfonyl, naphthylsulfonyl, ($C_1$-$C_{12}$)-alkoxy, $(C_1-C_6)$-alkoxy-$(C_1-C_6)$-alkoxy, —O—$[CH_2]_x$—$C_fH_{(2f+1-g)}F_g$, benzyloxy or phenoxy, where, in substituents which contain a phenyl or naphthyl ring, this is optionally monosubstituted by fluorine, chlorine, bromine, trifluoromethyl, $(C_1-C_6)$-alkyl, $(C_1-C_6)$-alkoxy, —O—$[CH_2]_x$—$C_fH_{(2f+1-g)}F_g$ or $(C_1-C_4)$-alkylsulfonyl, including the physiologically active salts.

Particularly preferred compounds of the formula I are, in addition, those in which m is 0, A is a —$CH_2$— group, $R^1$, $R^3$, $R^4$ and $R^5$ are hydrogen and $R^2$ is hydrogen, $(C_1-C_{12})$-alkyl, fluorine, chlorine, bromine, trifluoromethyl, $(C_1-C_{12})$-alkylsulfonyl, phenylsulfonyl, naphthylsulfonyl, $(C_1-C_{12}$alkoxy,)-alkoxy, $(C_1-C_6)$-alkoxy-$(C_1-C_6)$-alkoxy, —O—$[CH_2]_x$—$C_fH_{(2f+1-g)}F_g$, benzyloxy or phenoxy, where, in substituents which contain a phenyl or naphthyl ring, this is optionally monosubstituted by fluorine, chlorine, bromine, trifluoromethyl, $(C_1-C_6)$-alkyl, $(C_1-C_6)$-alkoxy, —O—$[CH_2]_x$—$C_fH_{(2f+1-g)}F_g$ or $(C_1-C_4)$-alkylsulfonyl, including the physiologically active salts.

Particularly preferred compounds of the formula I are furthermore those in which m is 0, A is a —$CH_2$— group, $R^1$, $R^2$ and $R^5$ are hydrogen, $R^4$ is hydrogen or chlorine and $R^3$ is hydrogen, fluorine, chlorine, $(C_1-C_{12})$-alkoxy, $(C_1-C_4)$-alkoxy-$(C_1-C_6)$-alkoxy, —O—$[CH_2]_x$—$C_fH_{(2f+1g)}F_g$, phenylsulfonyl, naphthylsulfonyl or phenoxy, where, in substituents which contain a phenyl or naphthyl ring, this optionally carries up to 3 identical or different substituents, preferably one substituent, from the series comprising fluorine, chlorine, bromine, trifluoromethyl, trifluoromethoxy, $(C_1-C_6)$-alkyl and $(C_1-C_6)$-alkoxy, including the physiologically active salts.

Particularly preferred compounds are furthermore those of the formula I in which m is 0, A is a —$CH_2$— group, $R^1$, $R^2$, $R^4$ and $R^5$ are hydrogen and $R^3$ is hydrogen, fluorine, chlorine, $(C_1-C_{12})$-alkoxy, $(C_1-C_4)$-alkoxy-$(C_1-C_6)$-alkoxy, —O—$[CH_2]_x$—$C_fH_{(2f+1-g)}F_g$, phenylsulfonyl, naphthylsulfonyl or phenoxy, where, in substituents which contain a phenyl or naphthyl ring, this optionally carries up to 3 identical or different substituents, preferably one substituent, from the series comprising fluorine, chlorine, bromine, trifluoromethyl, trifluoromethoxy, $(C_1-C_6)$-alkyl and $(C_1-C_6)$-alkoxy, including the physiologically active salts.

The invention furthermore relates to prodrugs to the compounds of the formula (I) which have the effect of inhibiting collagen biosynthesis in vivo owing to liberation of compounds of the formula I or salts thereof.

Finally, the invention also relates to prodrugs which have the effect of inhibiting prolyl 4-hydroxylase in vivo owing to liberation of compounds of the formula I or salts thereof.

Prodrug groupings are chemical groups which, in vivo, can be converted into the carboxylate group of the compounds of the formula I and/or can be split off from the amide N atom and/or can be converted into a quinoline ring.

The prodrug groups possible are known to the person of ordinary skill in the art.

The following prodrug groupings are mentioned in particular: for the carboxyl heptane/ethyl group, a prodrug selected from, e.g., ester, amide, hydroxymethyl, aldehyde and derivatives thereof, and for the quinoline N atom, a prodrug selected from, e.g., N-oxides and N-alkyl derivatives.

The invention relates to the use of compounds of the formula I and the physiologically tolerated salts for inhibition of collagen biosynthesis.

The invention relates to the use of compounds of the general formula I and the physiologically tolerated salts for inhibition of prolyl 4-hydroxylase.

The invention furthermore relates to the use of compounds of the formula I and the physiologically tolerated salts for the preparation of a pharmaceutical (medicament) against fibrotic diseases.

The invention furthermore relates to the use of compounds of the formula I and the physiologically tolerated salts for the preparation of a medicament against fibrotic diseases of the liver, the lungs and the skin.

Finally, the invention relates to the compounds of the formula I for use as medicaments.

The invention particularly relates to the compounds of the formula I for use as fibrosuppressants.

The invention furthermore relates to a process for the preparation of compounds of the formula I.

The compounds of the formula I in which

A—B is —$(CH_2)_{1-4}$—$CO_2H$ and m is 0 are prepared by 1.i.1) reacting quinoline-2-carboxylic acids of the formula II ($R^{11}$=H) with the amino esters of the formula III to give the amide esters of the formula IV, or 1.i.2.) reacting quinoline-2-carboxylic acid esters of the formula II ($R^{11}$=lower alkyl) under the conditions of aminolysis to give the compounds of the formula IV;

1.ii) liberating the compounds of the formulae Ib and V from the esters of the formulae IV and VI; and 1.iii) obtaining the compounds of the formulae Ib and VI from the compounds of the formulae V and IV by splitting off the hydroxyl-protective group $R^{10}$, and if appropriate b 1.iv) oxidizing the compounds of the formula Ib, IV, V or VI to give compounds of the formulae Ia, IVa, Va or VIa.

Suitable protecting groups (PG=Protecting Groups) such as are familiar to the person of ordinary skill in the art are, in particular, benzyl, p-methoxybenzyl, 3,4-dimethoxybenzyl, alkyl, methoxymethyl (MOM), methylthio, benzyloxymethyl (BOM), t-butyloxymethyl, 2-methoxyethoxymethyl (MEM) and tetrahydropyranyl (THP).

Further protecting groups and the conditions under which they are split off (conversion of compounds of the formula V into compounds of the formula I) are described by Theodoro W. Greene, Peter G. M. Wuts, in Protective Groups in Organic Synthesis, Second Edition 1991, John Wiley, Chapter 2 and 3, pages 10 to 174.

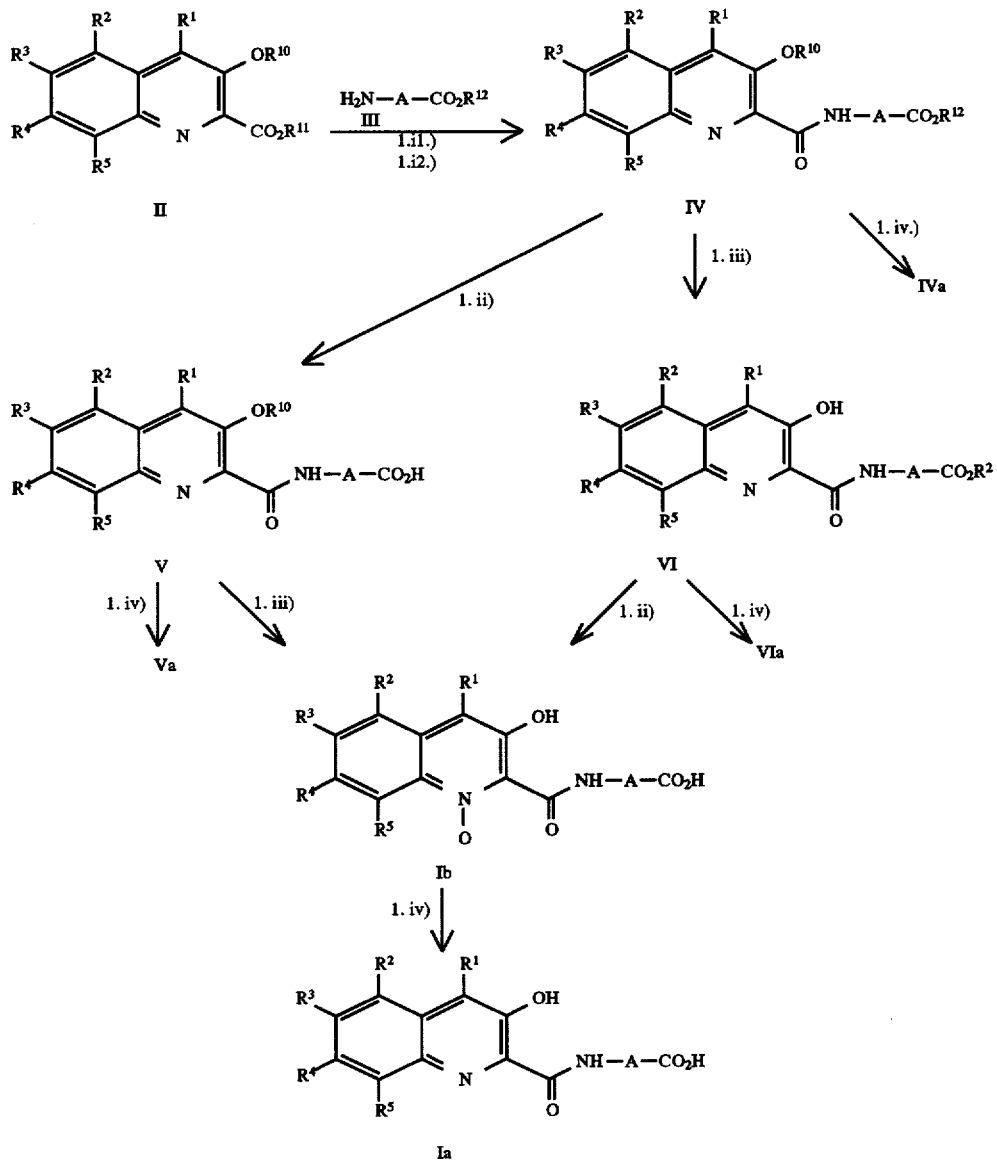

Equation 1.1. $R^{10}$= PG (Protecting Group)

$R^{11}$ = H, $(C_1-C_8)$-alkyl or benzyl
$R^{12}$ = H, $(C_1-C_8)$-alkyl or benzyl If the 3-OH function in the quinoline-2-carboxylic acids of the formula II a is present without a protecting group, these compounds can be reacted directly with the amino acid esters of the formula III to give the compounds of the formula VI.

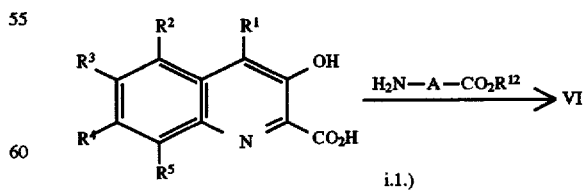

Equation 1.2., $R^{10}$ = H

To prepare the quinoline N-oxides of the formula Ia, the compounds of the formulae Ib, IV, V or VI are converted into their corresponding N-oxides of the formulae Ia, IVa, Va or VIa, and IVa, Va, and VIa are further treated analogously to equation 1.1.

Suitable processes for amide formation (reaction 1.i1.) are the methods of carboxyl activation and the condensation reactions known from peptide chemistry.

Reagents which can be used for activation of the carboxylic acids are the substances known to one of ordinary skill in the art, such as thionyl chloride, oxalyl chloride, pivaloyl chloride, chloroformic acid ester derivatives or N,N'-carbonyldiimidazole. The activated derivatives of the compounds of the formula II are reacted in situ, after their preparation, with the amide derivatives of the formula III.

A suitable condensing agent is, for example, the combination of N,N'-dicyclohexylcarbodiimide, 1-hydroxy-1H-benzotriazole and N-ethylmorpholine.

Suitable solvents are methylene chloride, carbon tetrachloride, butyl acetate, ethyl acetate, toluene, tetrahydrofuran, dimethoxyethane, 1,4-dioxane, acetonitrile, N,N-dimethylformamide, N,N-dimethylacetamide, dimethylsulfoxide, nitromethane and/or pyridine.

To prepare the compounds of the formula II, appropriately substituted quinolines having a protected hydroxyl function in the 3-position and an oxidizable group G in the 2-position are subjected to oxidation reactions (equation 2.1.).

Equation 2.1., G = oxidizable group,
for example $CH_3$, CHO, $CH_2OH$ or $CO-CH_3$

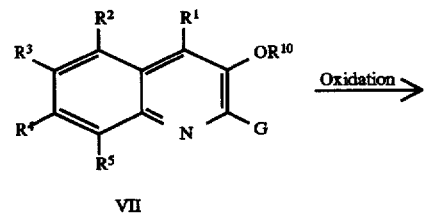

VII

Equation 2.1., G = oxidizable group,
for example $CH_3$, CHO, $CH_2OH$ or $CO-CH_3$

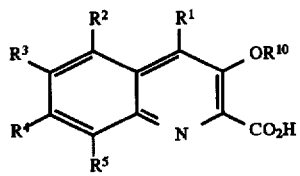

IIc

Variously substituted 3-hydroxy derivatives of the quinoline-2-carboxylic acids of the formula II are obtained in accordance with equation 2.2.

2.i) Substituted 2-nitrobenzoic acids of the formula VIII are treated by the customary methods of carboxylic acid activation and reacted with salts of acetyl-acetone to give the compounds of the formula IX.

2.ii) The compounds of the formula IX are cyclized with a base to give the 2-acetyl-3-hydroxyquinolines of the formulae Xa/b.

2.iii) The compounds of the formula Xa are reacted with a reagent $R^{10}$—X to give the hydroxyl-protected compounds of the formula XI.

2.iv) The compounds of the formula XI are oxidized to give the compounds of the formula II, preferably under the conditions of the haloform reaction.

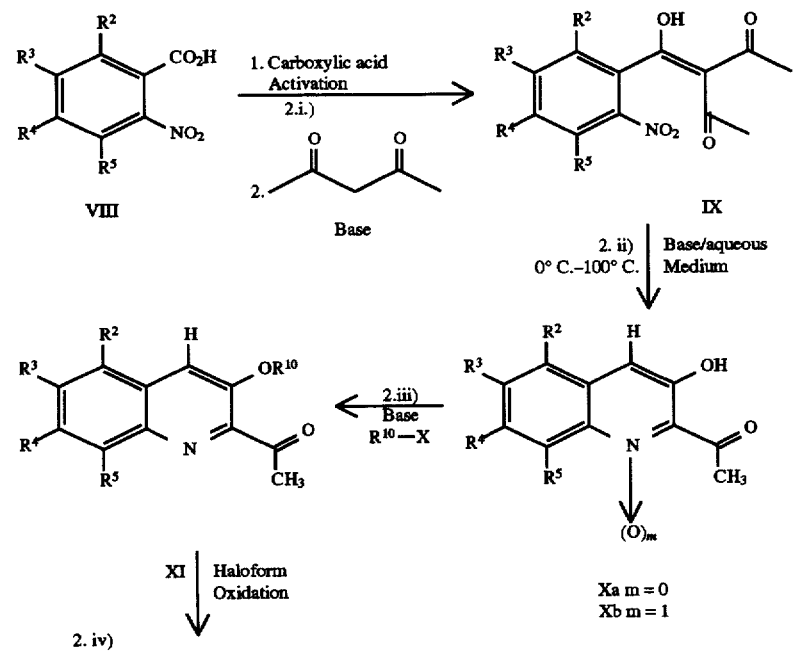

-continued
Equation 2.2. $R^1$ = H, $R^{10}$= PG (Protecting Group)

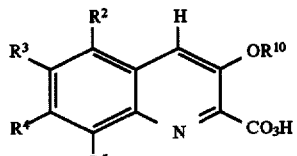

X Auxiliary group
for introduction of
the protecting group
$R^{10}$, for example
Cl, Br OTos, ...

IIb

The preparation of 3-(2-nitrobenzoyl)acetylacetone (formula IX; $R^2$—$R^5$=H) is known, J. Prakt. Chem. 1987, 329, page 1063.

The reaction of the compounds of the formula IX with aqueous potassium hydroxide solution to give the compounds of the formula Xa in which $R^2$, $R^4$ and $R^5$ are hydrogen and $R^3$ is hydrogen, methyl or chlorine is known from G. Tennant et al., J. Chem. Soc. Chem. Comm. 1975, 782.

It has now been found that the substituents $R^2$, $R^3$, $R^4$ and $R^5$ can be varied according to the invention to achieve the object described.

It has furthermore been found that the compounds of the formula XI can be oxidized in a mild manner under the conditions of the haloform reaction (aqueous alkali metal or alkaline earth metal hydroxide/bromine) to give the compounds of the formula II (IIb).

2-Nitrobenzoic acids of the formula VIII are commercially obtainable or known from the literature, or can be prepared by various synthesis methods—depending on the desired substitution pattern.

The compounds of the formulae II, IIa and IIb (intermediate products) are novel, with the following exceptions:

Compounds of the formula II in which—if $R^1$ to $R^5$ and $R^{11}$ are hydrogen—$R^{10}$ is benzyl or methyl, (or compounds of the formula IIb in which—if $R^2$ to $R^5$ are hydrogen—$R^{10}$ is benzyl or methyl) and compounds of the formula II in which—if $R^1$ to $R^5$ are hydrogen and $R^{11}$ is ethyl—$R^{10}$ is hydrogen, benzyl or p-toluenesulfonyl and compounds of the formula IIa in which—if $R^1$, $R^2$, $R^4$ and $R^5$ are hydrogen—$R^3$ is hydrogen or methoxy.

3-Benzyloxyquinoline-2-carboxylic acid is known from J. Am. Chem. Soc., Volume 115, No. 24, 1993, pages 11624–11625.

3-Hydroxyquinoline-2-carboxylic acid and methyl 3-methoxyquinoline-2-carboxylate are described in J. Antibiot. 1987, 40 (7), pages 953–960, and the former is also described in Chem. Pharm. Bull. 1967, 15 (5), pages 663–669.

3-Hydroxy-6-methoxyquinoline-2-carboxylic acid is described in J. Am. Chem. Soc., Vol. 103, No. 5, 1981, pages 1241–1243.

3-Methoxyquinoline-2-carboxylic acid is known from J. Am. Chem. Soc. 1960, pages 3371–3377.

Ethyl 3-hydroxyquinoline-2-carboxylate and ethyl 3-(p-toluenesulfonyloxy)quinoline-2-carboxylate are known from J. Chem. Soc. C. 1967, 4, pages 256–261.

Intermediate products of the formulae Xa and Xb are furthermore novel, with the following exceptions: Compounds of the formula Xa in which—if $R^2$, $R^4$ and $R^5$ are hydrogen—$R^3$ is hydrogen, methyl or chlorine. These known compounds of the formula Xa are described in J. Chem. Soc. Chem. Comm. 1975, pages 782 to 783.

The invention therefore also relates to the following intermediate products for the preparation of the compounds of the formula I:

Intermediate products of the formula II in which $R^1$ to $R^5$ have the meanings which apply to the compounds of the formula I, $R^{10}$ is H or an HO-protecting group (Protecting Group PG) and $R^{11}$ is hydrogen, ($C_1$–$C_8$)-alkyl or benzyl, with the exception of compounds of the formula II in which $R^{10}$ is benzyl or methyl if $R^1$ to $R^5$ and $R^{11}$ are hydrogen, and those compounds from the formula II in which $R^{10}$ is hydrogen, benzyl or p-toluenesulfonyl if $R^1$ to $R^5$ are hydrogen and $R^{11}$ is ethyl.

Intermediate products of the formula Xa in which $R^2$ to $R^5$ have the meanings which apply to the compounds of the formula I, with the exception of compounds of the formula Xa in which $R^3$ is hydrogen, methyl or chlorine if $R^2$, $R^4$ and $R^5$ are hydrogen.

Alkoxy- and benzyloxy-substituted quinoline systems of the present invention are prepared by alkylation of phenolic OH group(s) of 2-nitrobenzoic acids or derivatives thereof in which, after alkylation, the carboxylate group is introduced by oxidation of methyl, acetyl, hydroxymethyl or aldehyde groups or obtained by hydrolysis of an ester group, cf., for example, equation 3.1.

Equation 3.1.

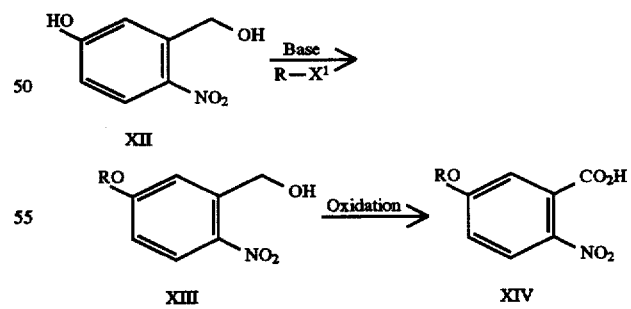

$X^1$ = Hal, tosylate or mesylate
R = ($C_1$–$C_{12}$)-alkyl, benzyl or ($C_1$–$C_6$)-alkoxy-($C_1$–$C_6$)alkyl 6-Aryloxyquinoline and 6-arylsulfonyl derivatives are accessible by nucleophilic aromatic substitution on 4-halo-2-nitrotoluenes XV and subsequent oxidation to give the corresponding 5-aryloxy (5-arylsulfonyl)-2-nitrobenzoic acids XVII, cf. equation 3.2.

Equation 3.2.

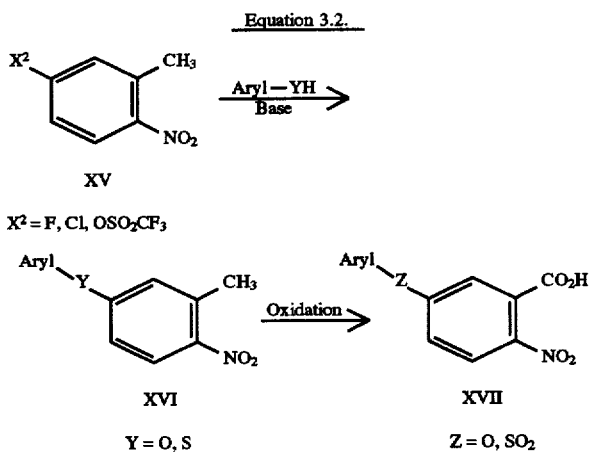

$X^2 = F, Cl, OSO_2CF_3$ $Y = O, S$         $Z = O, SO_2$

Another possibility is provided by nitration of appropriately substituted toluenes, benzoic acids, benzaldehydes or acetophenones. This method is preferably used if the substituents present direct the nitration exclusively or predominantly into the 2 position, cf., for example, equation 3.3.

Equation 3.3.

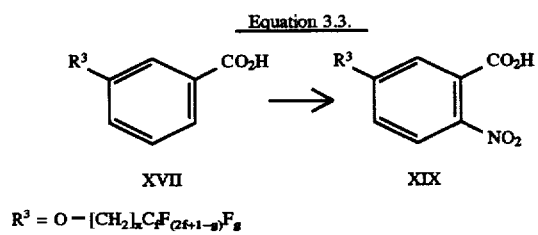

$R^3 = O-[CH_2]_kC_nF_{(2n+1-s)}F_s$

The compounds of the formula XIII and XVI were reacted with an oxidizing agent, preferably with $KMnO_4$ in an aqueous alkaline medium, to give the 2-nitrobenzoic acid derivatives.

The compounds of the formula I are inhibitors of prolyl 4-hydroxylase. The inhibition of this enzyme was determined as described by Kaule and Günzler in Annal. Biochem. 184, 291 to 297 (1990).

The compounds of the formula i according to the invention furthermore have valuable pharmacological properties and show, in particular, an antifibrotic activity.

The antifibrotic action can be determined in the model of fibrosis of the liver induced by carbon tetrachloride. For this, rats are treated twice weekly with $CCl_4$ (1 ml/kg), dissolved in olive oil. The test substance is administered daily, if appropriate even twice daily, perorally or intraperitoneally - dissolved in a suitable tolerated solvent. The extent of the fibrosis of the liver is determined histologically and the content of collagen in the liver is analyzed by hydroxyproline determination—as described by Kivirikko et al. (Anal. Biochem. 19, 249 et seq. (1967)). The activity of the fibrogenesis can be determined by radioimmunological determination of collagen fragments and procollagen peptides in the serum. The compounds according to the invention are active in this model in a concentration of 1 to 100 mg/kg.

The activity of the fibrogenesis can be determined by radioimmunological assay of the N-terminal propeptide of type III collagen or of the N- or C-terminal crosslinking domain of type IV collagen (7s collagen or type IV collagen $NC_1$) in the serum.

For this purpose, the hydroxyproline, procollagen III peptide, 7s collagen and type IV collagen NC concentrations in the liver of a) untreated rats (control)
b) rats to which carbon tetrachloride was administered ($CCl_4$ control)
c) rats to which first $CCl_4$ and then a compound according to the invention was administered were measured (this test method is described by Rouiller, C., experimental toxic injury of the liver; in The Liver, C. Rouiller, Volume 2, 5. 335 to 476, New York, Academic Press, 1964).

An activity of the compounds according to the invention can furthermore be detected in the following systems.

Inhibition of hepatic prolyl 4-hydroxylase in vivo:

This model is used for detection of acute inhibition of prolyl 4-hydroxylase in vivo. For this, the test substance and the corresponding vehicle are administered (intraperitoneally, intravenously, perorally) to rats of both sexes (healthy and with induced fibrosis of the liver) and, after administration of the substance, $^{14}$C-L-proline 250 µCi/kg of body weight) is administered intraperitoneally. $^{14}$C-L-Proline (250 µCi/kg of body weight) is then administered again intraperitoneally. Finally, the animals are exsanguinated under pentobarbital anesthesia and the liver is removed. The hepatic collagen was purified by pepsin digestion and fractional ammonium sulfate precipitation in accordance with published protocols (Ref. 1, 2). The purified liver collagen was hydrolyzed and the content of $^{14}$C-hydroxyproline and $^{14}$C-proline was determined by amino acid analysis by means of ion exchange chromatography. inhibition of prolyl 4-hydroxylase can be seen from a reduction in the quotient $^{14}$C-hydroxyproline/[$^{14}$C-hydroxyproline+$^{14}$C-proline]. 2,2'-Dipyridyl is used as the reference substance. (Ref. 1: Chojkier, M. 1986. Hepatocyte collagen production in vivo in normal rats. J. Clin. Invest. 78:333–339 and Ref. 2: Ogata I. et al. 1991. Minor contribution of hepatocytes to collagen production in normal and early fibrotic livers. Hepatology 14: 361–367).

Inhibition of prolyl 4-hydroxylase in cell cultures:

The following cell types are used for testing prolyl 4-hydroxylase inhibitors in cell cultures: Normal human dermal fibroblasts (NHDF), rat liver epithelial cells (Ref. 1) and primary fat storing cells from the rat liver (Ref. 2). For this, the cells are cultured in the presence of inhibitors. At the same time, the collagen newly synthesized during this period is labeled metabolically by 4-$^3$H-L-proline and $^{14}$C-proline. The influence of the test substances on the degree of hydroxlyation of the collagen is then determined in accordance with the method of Chojkier et al. (Ref. 3). 2,2'-Dipyridyl is employed as the reference substance. (1.: Schrode, W., Mecke, D., Gebhard, R. 1990. Induction of glutamine synthetase in periportal hepatocytes by co-cultivation with a liver epithelial cell line. Eur. J. Cell. Biol. 53: 35–41, 2. Blomhoff, R., Berg T. 1990. Isolation and cultivation of rat liver stellate cells. Methods Enzymol. 190: 59–71 and 3.: Chojkier, M. Peterkofsky, B. Bateman J. 1980. A new method for determining the extent of proline hydroxylation by measuring changes in the ration of [4-$^3$H] :[$^{14}$C] proline in collagenase digests. Anal. Biochem. 108: 385–393).

The compounds of the formula I can be used as medicaments in the form of pharmaceutical preparations which comprise them, if appropriate with tolerated pharmaceutical excipients. The compounds can be used as medicines, for example in the form of pharmaceutical preparations, which comprise these compounds as a mixture with a pharmaceutical, organic or inorganic excipient suitable for enteral, percutaneous or parenteral administration, such as, for example, water, gum arabic, gelatin, lactose, starch, magnesium stearate, talc, vegetable oils, polyalkylene glycols, petroleum jelly and the like.

For this purpose, they can be administered orally in doses of 0.1 to 25 mg/kg/day, preferably 1 to 5 mg/kg/day, or parenterally in doses of 0.01 to 5 mg/kg/day, preferably 0.01 to 2.5 mg/kg/day, in particular 0.5 to 1.0 mg/kg/day. In severe cases, the dosage can also be increased. However, lower doses are also sufficient in many cases. These data relate to an adult weighing about 75 kg.

In the examples described below, the compounds of the formula I according to the invention are understood as meaning substituted quinoline-2-carboxylic acid N-(carboxymethyl)amides (quinoline-2-carboxylic acid glycinamides). The term substituted N-((quinolin-2-yl) carbonyl)-glycines is used in parallel.

The examples are intended to illustrate, but not to limit the claimed invention.

EXAMPLE 1

3-Hydroxyquinoline-2-carboxylic acid N-(carboxymethyl)amide a) 3-(2-Nitrobenzoyl)acetylacetone was obtained from acetylacetone and 2-nitrobenzoyl chloride, melting point 69° C.; cf. J. Prakt. Chem. 1987, 329, page 1063, 29% yield.

b) 2-Acetyl-3-hydroxyquinoline was obtained from the product a) under basic conditions (KOH/water, Smiles rearrangement), melting point 105° C.; cf. J. Chem. Soc. Chem. Comm. 1975, 782; 53% yield.

c) 2-Acetyl-3-benzyloxyquinoline was obtained from the product b) with benzyl bromide (potash/acetone), 52% yield.

$^1$H-NMR (CDCl$_3$): δ=2.89 (2, 3H), 5.25 (s, 2H), 7.38 (m, 3H), 7.58 (m, 5H), 7.70 (m, 1H), 8.08 (m, 1H).

d) 3-Benzyloxyquinoline-2-carboxylic acid was obtained from the product c) with potassium hypochlorite (dioxane/water), oily crude product, 47% yield, $^1$H-NMR (CDCl$_3$): δ=5.40 (s, 2H), 7.40 (m, 3H), 7.63 (m, 4H), 7.75 (m, 2H), 8.07 (m, 1H).

e) 3-Benzyloxyquinoline-2-carboxylic acid N-((benzyloxycarbonyl)methyl)amide was obtained from the product d) with triethylamine/ethyl chloroformate (mixed anhydride method) and glycine benzyl ester tosylate, oily crude product, 64% yield, $^1$H-NMR (CDCl$_3$): δ=4.40 (d, 2H), 5.25 (s, 2H), 5.35 (s, 2H), 7.10 to 7.75 (m, 14H), 8.10 (m, 1H), 7.28 (t, 1H).

f) The title compound was obtained by hydrogenating the product e) in methanol with Pd/C (10%) in a duck-shaped shaking vessel, melting point 191° C. (from aqueous hydrochloric acid), 40% yield.

EXAMPLE 2

N-((3-Hydroxy-6-methoxyquinolin-2-yl)carbonyl) glycine a) 3-(5-Methoxy-2-nitrobenzoyl)acetylacetone 28 g of crude product was obtained from 19.75 g of 5-methoxy-2-nitrobenzoic acid with oxalyl chloride and Mg acetylacetonide analogously to Example 4c).

b) 2-Acetyl-3-hydroxy-6-methylquinoline 28 g (0.1 mol) of the above crude product were heated under reflux in 250 ml of 20% strength aqueous KOH solution for 30 minutes. The mixture was worked up as under Example 4d), the crude product was chromatographed over silica gel with n-heptane/ethyl acetate (1:1) and 5.1 g of product was crystallized from corresponding fractions with diisopropyl ether, melting point 124°–126° C.

c) 2-Acetyl-3-benzyloxy-6-methoxyquinoline, from the above compound by alkylation with benzyl bromide, melting point 100°–102° C. (from diisopropyl ether).

d) 3-Benzyloxy-6-methoxyquinoline-2-carboxylic acid 1.2 g (4 mmol) of the above acetyl compound, dissolved in 5 ml of 1,4-dioxane, were added dropwise to a solution of 1.6 g of NaOH (40 mmol) in 8 ml of water, to which 0.6 ml (12 mmol) of bromine had been added at 5°–10° C. After a little diethyl ether had been added and the organic phase had been separated off, a solution of 0.4 g of sodium disulfite in 6 ml of water was added to the alkaline solution, the mixture was concentrated in vacuo, the residue was taken up in 8 ml of water, the pH was brought to 2 with concentrated HCl, while cooling, and the product which had crystallized was filtered off with suction and dried, 0.83 g, melting point 272°–275° C. (sintering 90° C.).

e) N-((3-Benzyloxy-6-methoxyquinolin-2-yl)carbonyl) glycine 1-butyl ester 0.83 g (2.7 mmol) of the above carboxylic acid were reacted with 0.82 g (2.7 mmol) of glycine butyl ester tosylate, 1.1 ml (8.1 mmol) of NEM, 0.405 g (3 mmol) of HOBT and 1.14 g (2.7 mmol) of CMC in 200 ml of anhydrous methylene chloride analogously to Example 4g). The crude product was chromatographed over silica gel with ethyl acetate. 0.8 g of product was crystallized from corresponding fractions with diisopropyl ether, melting point 90°–92° C.

f) N-((3-Benzyloxy-6-methoxyquinolin-2-yl)carbonyl) glycine 0.5 g (1.2 mmol) of the above ester was hydrolyzed in 1.5N methanolic sodium hydroxide solution, 0.45 g of product, melting point 118° C. (sintering at 105° C., from aqueous hydrochloric acid).

g) The title compound was obtained by hydrogenating 0.4 g (1.1 mmol) of the above benzyl compound in methanol/tetrahydrofuran (1:1) with Pd/C (10%) in a duck-shaped shaking vessel. After the catalyst had been filtered off with suction and the filtrate concentrated in vacuo, the residue was crystallized with diethyl ether, 0.16 g, melting point 258°–260° C.

EXAMPLE 3

N-((6-(1-Hexyloxy)-3-hydroxyquinolin-2-yl) carbonyl)glycine

EXAMPLE 4

N-((6-(1-Butyloxy)-3-hydroxyquinolin-2-yl) carbonyl)glycine a) 5-(1-Butyloxy)-2-nitrobenzyl alcohol 5.1 g (30 mmol) of 5-hydroxy-2-nitrobenzyl alcohol were stirred with 2.5 g (18 mmol) of potassium carbonate and 25 ml of N,N-dimethylacetamide at 70°–80° C. for 30 minutes. After cooling to 20° C., 3.9 ml (36 mmol) of 1-butylbromide were added dropwise and the mixture was stirred at 90° C. for 2 hours. After cooling, the reaction mixture was concentrated in vacuo, the residue was treated with water and the pH was brought to 7 with 2N HCl. The oil obtained crystallizes after about 30 minutes; the product was filtered off with suction, washed with water and dried; 6 g, melting point 47°–49° C.

b) 5-(1-Butyloxy)-2-nitrobenzoic acid 0.5 g (10 mmol) of potassium hydroxide was dissolved in 40 ml of water, 2.2 g (10 mmol) of the above alcohol were added at 20° C., while stirring, the mixture was heated to 70°–80° C. and 3.16 g (20 mmol) of potassium permanganate were added in portions. After the mixture had been stirred at 60°–70° C. for 30 minutes, it was filtered hot with suction, the residue on the filter was washed with hot water, the filtrate was concentrated to 20 ml and half-concentrated hydrochloric acid was added down to a pH of 1–2. The oil which separates off crystallized after 1 hour. The product was filtered off with suction and washed with water, 2 g, melting point 82°–84° C.

c) 3-(5-(1-Butyloxy)-2-nitrobenzoyl)acetylacetone 1. 5-(1-Butyloxy)-2-nitrobenzoyl chloride 3 drops of N,N-dimethylformamide and, dropwise, 7 ml of oxalyl chloride (in 12 ml of tetrahydrofuran) were added to 12 g (50 mmol) of the above benzoic acid in 90 ml of anhydrous tetrahydrofuran at 5° C.

The mixture was allowed to warm to room temperature and was stirred for 1 hour and concentrated in vacuo, and the residue was taken up in 25 ml of anhydrous toluene.

2. Magnesium acetylacetonide 1.23 g (50 mmol) of magnesium chips were heated under reflux with a crystal of iodine in 20 ml of anhydrous ethanol and 2.5 ml of xylene for 8 hours. The mixture was then concentrated in vacuo, the residue was taken up in 100 ml of anhydrous toluene, 5.2 ml (50 mmol) of freshly distilled acetylacetone were added dropwise at 20° C. and the mixture was stirred for 30 minutes.

This solution of magnesium acetylacetonide in toluene was cooled to 0° C. and the solution, prepared under 1, of the acid chloride was added dropwise, while stirring. The mixture was stirred at 0° C. for 1 hour and left to stand overnight at 20° C., 200 ml of ice-water and concentrated hydrochloric acid to pH 1 were added, the mixture was stirred for 30 minutes and the organic phase was washed with water and dried to give, after concentration in vacuo, 14 g of oily crude product.

d) 2-Acetyl-6-(1-butyloxy)-3-hydroxyquinoline 14 g (43.6 mmol) of the above product were heated under reflux in 150 ml of 20% strength aqueous KOH solution for 30 minutes. After cooling, the pH was brought to 1–2 with half-concentrated hydrochloric acid, while stirring, the mixture was extracted three times with methylene chloride, the organic phase was dried and concentrated in vacuo and the residue was chromatographed over silica gel with n-heptane/ethyl acetate (3:1). 2.5 g of product were crystallized from corresponding fractions with petroleum ether, melting point 71°–73° C.

e) 2-Acetyl-3-benzyloxy-6-(1-butyloxy)quinoline 2.5 g (about 10 mmol) of the above product were reacted with 1.38 g (10 mmol) of potassium carbonate and 1.2 ml (10 mmol) of benzyl bromide in 30 ml of N,N-dimethylacetamide (1 hour at 75°–80° C.). 2.2 g of product were obtained, melting point 91°–93° C. (from diisopropyl ether).

f) 3-Benzyloxy-6-(1-butyloxy)quinoline-2-carboxylic acid (haloform oxidation)

0.45 ml (9 mmol) of bromine was added to a solution of 1.2 g (30 mmol) of NaOH in 6 ml of water at 5°–10° C., while stirring. A solution of 1.05 g (3 mmol) of the above acetyl compound, dissolved in 5 ml of 1,4-dioxane, was then added dropwise. The mixture was stirred at 20° C. for a further hour and extracted with 5 ml of diethyl ether, the organic phase was concentrated, the residue was treated with 2N aqueous HCl, the mixture was decanted, the residue was dissolved in ethyl acetate, the solution was dried with magnesium sulfate and concentrated and the residue was crystallized with diisopropyl ether. 0.8 g was obtained, melting point 108°–110° C.

g) N-((3-Benzyloxy-6-(1-butyloxy) quinolin-2-yl) carbonyl)glycine 1-butyl ester 0.8 g (2.28 mmol) of the above quinoline-2-carboxylic acid was dissolved in 200 ml of anhydrous methylene chloride, 0.74 g (2.43 mmol) of glycine 1-butyl ester tosylate, 1.1 ml (8.1 mmol) of N-ethylmorpholine (NEM), 0.405 g (3 mmol) of 1-hydroxybenzotriazole (HOBT) and 1.0 g (2.43 mmol) of N-cyclohexyl-N'-(2-morpholinoethyl) carbodiimide-methyl-p-toluenesulfonate (CMC) were added in succession and the mixture was stirred at 20° C. for 30 hours.

The reaction solution was then shaken with 2N aqueous HCl, dilute NaOH was added to a precipitate, the mixture was extracted with diethyl ether, the combined organic phases were extracted with aqueous Na bicarbonate solution, dried and concentrated and the residue was chromatographed over silica gel with n-heptane/ethyl acetate (2:1). After corresponding fractions had been concentrated and treated with diisopropyl ether, 0.55 g of product was obtained, melting point 99°–101° C.

h) The title compound was obtained by hydrolyzing 0.5 g of the above glycine ester with 50 ml of 1N methanolic NaOH at 20° C. The mixture was concentrated in vacuo, water was added to the residue, the mixture was extracted with diethyl ether, the aqueous, oily phase was acidified after addition of tetrahydrofuran, while cooling, and concentrated in vacuo, and the aqueous phase was extracted with methylene chloride, dried and concentrated to give 0.46 g of oily product. 0.3 g of the glycine obtained was dissolved in 75 ml of tetrahydrofuran, Pd/C (10%) was added and the glycine was hydrogenated in a duck-shaped shaking vessel. The catalyst was filtered off with suction, the filtrate was concentrated and the residue was crystallized with diisopropyl ether. 140 mg of the title compound were obtained as a colorless crystalline substance, melting point 180°–182° C.

EXAMPLE 5

N-((6-Ethyloxy-3-hydroxyquinolin-2-yl)carbonyl) glycine

EXAMPLE 6

N-((3-Hydroxy-6-(1-octyloxy)quinolin-2-yl) carbonyl)glycine

The title compound was obtained analogously to Example 4:

a) 2-Nitro-5-(1-octyloxy)benzyl alcohol The oil obtained after treatment with 1N hydrochloric acid slowly crystallized completely, melting point 55°–57° C.

b) 2-Nitro-5-(1-octyloxy)benzoic acid, oily crude product.

c) 3-(2-Nitro-5-(1-octyloxy)benzoyl)acetylacetone; oily product (after chromatography over silica gel with n-heptane/ethyl acetate (3:1)).

d) 2-Acetyl-3-hydroxy-6-(1-octyloxy)quinoline, oily product, which solidifies on standing.

e) 2-Acetyl-3-benzyloxy-6-(1-octyloxy)quinoline; oily product which crystallized completely on standing.

f) 3-Benzyloxy-6-(1-octyloxy)quinoline-2-carboxylic acid; melting point 145° C. (with decomposition, from aqueous hydrochloric acid/tetrahydrofuran).

g) N-((3-Benzyloxy-6-(1-octyloxy)quinolin-2-yl)-carbonyl)glycine benzyl ester; melting point 93°–95° C. (from petroleum ether).

h) The title compound was obtained by hydrogenating the above benzyl compound with Pd/C; melting point 153°–155° C. (from petroleum ether).

EXAMPLE 7

N-((6-(1-Decyloxy)-3-hydroquinolin-2-yl)carbonyl) glycine

EXAMPLE 8

N-((3-Hydroxy-6-((2,2,2-trifluoroethyl)oxy) quinolin-2-yl)carbonyl)glycine hydrochloride 0.5 g (1.3 mmol) of N-((7-chloro-3-hydroxy-6-(2,2,2-trifluoroethyloxy)quinolin-2-yl)carbonyl)glycine (title compound from Example 31) was dissolved in 26 ml of methanolic formic acid (4.4% strength), and a further 26 ml of methanolic formic acid were added at 20° C. After addition of 0.5 g of Pd/C (10%), the mixture was stirred at 20° C. for 1 hour, the catalyst was filtered off, the filtrate was concentrated and the residue was crystallized with diisopropyl ether. 250 mg of product were obtained, melting point>300° C. (sintering at 207° C.).

EXAMPLE 9

N-((3-Hydroxy-6-((2,2,3,3,3-pentafluoropropyl)oxy) quinolin-2-yl)carbonyl)glycine

EXAMPLE 10

N-((6-((2,2,3,3,4,4,4-Heptafluorobutyl)oxy)-3-hydroxyquinolin-2-yl)carbonyl)glycine

EXAMPLE 11

N-((6-Chloro-3-hydroxyquinolin-2-yl)carbonyl) glycine a) 2-Acetyl-6-chloro-3-hydroxyquinoline, cf. J. Chem. Soc. Chem. Comm. 1975, 782.

b) 2-Acetyl-3-benzyloxy-6-chloroquinoline 5.0 g (22.5 mmol) of the above chloroquinoline were dissolved in 50 ml of N,N-dimethylacetamide, the solution was stirred with 3.4 g (25 mmol) of potassium carbonate at 70°–80° C. for 30 minutes, 3.1 ml (25 mmol) of benzyl bromide were added dropwise at 20° C. and the mixture was stirred at 90° C. for 2 hours. After working up, the residue was chromatographed over silica gel with n-heptane/ethyl acetate (4:1) and 4.2 g of product were crystallized from corresponding fractions with diisopropyl ether, melting point 107°–110° C.

c) 3-Benzyloxy-6-chloroquinoline-2-carboxylic acid 2.1 g (6.7 mmol) of the above acetyl compound, dissolved in 7 ml of 1,4-dioxane, were added dropwise to a solution of 1 ml (20 mmol) of bromine in aqueous sodium hydroxide solution (from 2.7 g (6.7 mmol) in 13.5 ml of water) at 0° C. After working up, 1.2 g of product were obtained, melting point 90°–93° C. (sintering from 80° C., from aqueous hydrochloric acid).

d) N-((3-Benzyloxy-6-chloroquinolin-2-yl)carbonyl) glycine 1-butyl ester

The product was obtained analogously to Example 4 g) from 1.1 g (3.3 mmol) of the above quinolinecarboxylic acid and the coupling reagents NEM, HOBT, CMC and glycine 1-butyl ester tosylate, 0.75 g, melting point 121°–123° C. (from diisopropyl ether).

e) The title compound was obtained by hydrolyzing 0.3 g (0.75 mmol) of the above glycine ester in 25 ml of 1N methanolic sodium hydroxide solution at 20° C. for 1 hour. 0.3 g of the resinous Na salt was isolated, 12.5 ml of 48% strength aqueous HBr were added and the mixture was stirred at a bath temperature of 80°–85° C. for 1 hour. After the mixture had been concentrated in vacuo, the crystalline residue was extracted with tetrahydrofuran, the extract was concentrated in vacuo and the residue was crystallized with diisopropyl ether. 0.16 g of the title compound was obtained, melting point 224° C. (with decomposition).

EXAMPLE 12

N-((6-Bromo-3-hydroxyquinolin-2-yl)carbonyl) glycine

EXAMPLE 13

N-((3-Hydroxy-6-(phenylsulfonyl)quinolin-2-yl) carbonyl)glycine a) 2-Nitro-5-(phenylsulfonyl)toluene 4 g (100 mmol) of NaOH were dissolved in 150 ml of anhydrous ethanol, while stirring and heating, 10.3 ml (100 mmol) of thiophenol were added dropwise at 20° C. and, after 10 minutes, 15.5 g (12.2 ml; 100 mmol) of 5-fluoro-2-nitrotoluene, dissolved in 20 ml of ethanol, were added dropwise. After 30 minutes at 20° C., the mixture was heated under reflux for 30 minutes and filtered hot. After trituration, crystallization started. After addition of water, the product was filtered off with suction and dried; 19 g of 2-nitro-5-phenylthiotoluene, melting point 70°–71° C. Oxidation was then carried out with m-chloroperbenzoic acid in methylene chloride; 20.5 g of product, melting point 108°–10° C. (from petroleum ether).

b) 2-Nitro-5-(phenylsulfonyl)benzoic acid 15 g (55 mmol) of 2-nitro-5-phenylsulfonyltoluene were suspended in 210 ml of pyridine/water (1:2), and 79 g (500 mmol) of potassium permanganate were added in portions, in each case until decoloration occurred, under reflux. The mixture was then filtered hot with suction and the residue was rinsed three times with hot water. Starting material (2.8 g) which had precipitated out in the filtrate was recovered. The second filtrate was concentrated, 200 ml of water were added, the mixture was extracted with diethyl ether and the aqueous phase was brought to pH 1 with half-concentrated aqueous HCl, while cooling. The product which had precipitated out was filtered off with suction and dried; 9 g, melting point 210°–212° C.

c) 3-(2-Nitro-5-(phenylsulfonyl)benzoyl)acetylacetone 9.4 g of product were obtained from 9 g (30 mmol) of the above substance with oxalyl chloride and magnesium acetylacetonide analogously to Example 4c), melting point 143°–145° C. (sintering at 140° C., from diisopropyl ether).

d) 2-Acetyl-3-hydroxy-6-(phenylsulfonyl)quinoline 9.5 g of the above compound were introduced into 95 ml of aqueous potassium hydroxide solution (20% strength) at 20° C., while stirring, a clear solution forming after 45 minutes. After 90 minutes, the pH was brought to 1 with half-concentrated HCl, while cooling, and the crude product was filtered off with suction. This was chromatographed over silica gel with n-heptane/ethyl acetate (3:1). 1.5 g of product were isolated from corresponding fractions, melting point 179°–180° C.

e) 2-Acetyl-3-benzyloxy-6-(phenylsulfonyl)quinoline 1.5 g (4.6 mmol) of the above compound were reacted with 0.63 g (4.6 mmol) of potassium carbonate and 0.55 ml (4.6 mmol) of benzyl bromide in 50 ml of diethyl ketone (heating under reflux for 3 hours). 2.0 g of product were obtained, melting point 160°–162° C. (from water).

f) 3-Benzyloxy-6-(phenylsulfonyl)quinoline-2-carboxylic acid 2.0 g (4.8 mmol) of the above acetyl compound were subjected to the haloform reaction analogously to Example 4 f). 1.4 g of product, which was reacted further, were obtained.

g) N-((3-Benzyloxy-6-(phenylsulfonyl)quinolin-2-yl)carbonyl)glycine benzyl ester 1.4 g (3.3 mmol) of the above carboxylic acid were reacted with glycine benzyl ester tosylate, N-ethylmorpholine, 1-hydroxy-1H-benzotriazole and CMC analogously to Example 4 g). 1.1 g of product were obtained, melting point 165°–167° C. (from diethyl ether).

h) The title compound was obtained by hydrogenating 1.1 g (1.9 mmol) of the above benzyl ester in tetrahydrofuran with Pd/C (10%) in a duck-shaped shaking vessel. 0.5 g of colorless product was obtained, melting point 196°–198° C. (from diisopropyl ether).

EXAMPLE 14

N-((6-((4-Fluorophenyl)sulfonyl)-3-hydroxyquinolin-2-yl)carbonyl)glycine

EXAMPLE 15

N-((6-Benzyloxy-3-hydroxyquinolin-2-yl)carbonyl)glycine

EXAMPLE 16

N-((6-(4-Fluorobenzyloxy)-3-hydroxyquinolin-2-yl)carbonyl)glycine

EXAMPLE 17

N-((7-Butyloxy-3-hydroxyquinolin-2-yl)carbonyl)glycine

EXAMPLE 18

N-((7-Benzyloxy-3-hydroxyquinolin-2-yl)carbonyl)glycine

EXAMPLE 19

N-((6-(cis-3-Hexenyl-1-oxy)-3-hydroxyquinolin-2-yl)carbonyl)glycine

EXAMPLE 20

N-((6-(trans-3-Hexenyl-1-oxy)-3-hydroxyquinolin-2-yl)carbonyl)glycine

EXAMPLE 21

N-((3-Hydroxy-6-trifluoromethoxyquinolin-2-yl)carbonyl)glycine a) 2-Nitro-5-trifluoromethoxybenzoic acid 29.7 ml of nitric acid were added dropwise to 76.5 ml of concentrated sulfuric acid, while cooling and stirring, and 9.0 g (43.7 mmol) of 3-trifluoromethoxybenzoic acid were then added. The reaction mixture was heated at 50°–55° C. for 1 hour and, after cooling, was poured onto ice, and the residue was filtered off with suction to give, after drying, 8.8 g of product, melting point 90°–93° C. (sintering at 85° C.).

b) 3-(2-Nitro-5-trifluoromethoxybenzoyl)acetylacetone was obtained from 8.8 g (35 mmol) of the above 2-nitro-5-trifluoromethoxybenzoic acid analogously to Example 4c), 13 g of oily crude product.

c) 2-Acetyl-3-hydroxy-6-trifluoromethoxyquinoline 11.5 g (34.5 mmol) of the above product were introduced into 105 ml of 20% strength aqueous potassium hydroxide solution at 20° C., while stirring, and the mixture was heated under reflux for 30 minutes. After cooling, the pH was brought to 1 with half-concentrated aqueous HCl, the precipitate was filtered off with suction and the crude product (11 g) was chromatographed over silica gel with n-heptane/ethyl acetate. Corresponding fractions were concentrated and crystallized with petroleum ether; 5.1 g, melting point 87°–88° C. 0.45 g of the corresponding N-oxide was obtained as a by-product, melting point 190°–191° C.

d) 2-Acetyl-3-benzyloxy-5-trifluoromethoxyquinoline 5.0 g (18.4 mmol) of the above compound were reacted with 2.2 ml (18.4 mmol) of benzyl bromide in diethyl ketone analogously to Example 4e); 5.6 g of product, melting point 90°–92° C. (from petroleum ether).

e) 3-Benzyloxy-5-trifluoromethoxyquinoline-2-carboxylic acid 2.9 g of product were obtained from 2.7 g (7.5 mmol) of the above compound with 1.15 ml (22.5 mmol) of bromine in sodium hydroxide solution/1,4-dioxane, melting point 286° C. (with evolution of gas, from the reaction solution).

f) N-((3-Benzyloxy-5-trifluoromethoxyquinolin-2-yl)carbonyl)glycine benzyl ester 1.35 g of product were obtained from 1.8 g (5 mmol) of the above quinoline-2-carboxylic acid, 1.7 g (5 mmol) of glycine benzyl ester tosylate, 2.7 ml (20 mmol) of NEM, 0.74 g (5.5 mmol) of HOBT and 2.1 g (5 mmol) of CMC analogously to Example 4 g), melting point 123°–124° C. (from diisopropyl ether).

g) The title compound was obtained by hydrogenating 1.35 g (2.65 mmol) of the above glycine benzyl ester in 100 ml of tetrahydrofuran with Pd/C (10%) in a duck-shaped shaking vessel. After the catalyst had been filtered off with suction and the filtrate concentrated, the residue was crystallized with petroleum ether to give 0.7 g of product, melting point 192°–194° C.

Examples 22, 23 and 24 were obtained from corresponding precursors analogously to Example 21.

EXAMPLE 22

N-((6-((Heptafluoropropyl)oxy)-3-hydroxyquinolin-2-yl)carbonyl)glycine

EXAMPLE 23

N-((3-Hydroxy-6-((nonafluorobutyl)oxy)quinolin-2-yl)carbonyl)glycine

EXAMPLE 24

N-((3-Hydroxy-6-((pentafluoroethyl)oxy)quinolin-2-yl)carbonyl)glycine

EXAMPLE 25

N-((6-(3-(Ethyloxy)-1-propyloxy)-3-hydroxyquinolin-2-yl)carbonyl)glycine a) 5-(3-Ethyloxy)-1-propyloxy)-2-nitro-benzyl alcohol 5.0 g (=30 mmol) of 5-hydroxy-2-nitrobenzyl alcohol were reacted with 7.1 g (about 40 mmol) of 3-ethoxy-1-propyl bromide (prepared from 8.3 g (9.2 ml, 80 mmol) of 3-ethoxy-1-propanol and 15.3 ml (160 mmol) of phosphorus tribromide in methylene chloride) analogously to Example 4a); 6.1 g of crude product.

b) 5-(3-(Ethyloxy)-1-propyloxy)-2-nitrobenzoic acid 8.1 g of product were obtained from 10.2 g (40 mmol) of the above alcohol analogously to Example 4b), melting point 109°–111° (from aqueous hydrochloric acid).

c) 3-(5-(3-Ethyloxy)-1-propyloxy)-2-nitrobenzoyl)acetyl-acetone 10.3 g of oily crude product were obtained from 10.2 g (about 40 mmol) of the above benzoic acid analogously to Example 4c), after chromatography over silica gel with n-heptane/ethyl acetate (1:1).

d) 2-Acetyl-6-(3-ethyloxy-1-propyloxy)-3-hydroxyquinoline was obtained by reaction of 10 g of the above compound in 100 ml of 20% strength aqueous potassium hydroxide solution (40 minutes, 60° C.), 2.8 g, melting point 62°–64° C. (from n-heptane/ethyl acetate (3:1)).

e) 2-Acetyl-3-benzyloxy-6-(3-ethyloxy-1-propyloxy)quinoline 2.8 g (10 mmol) of the above compound were reacted with 1.4 g of potassium carbonate and 1.2 ml (10 mmol) of benzyl bromide in 80 ml of diethyl ketone, 3.8 g of oily product after chromatography over silica gel with n-heptane/ethyl acetate (1:1).

f) 3-Benzyloxy-6-(3-ethyloxy-1-propyloxy)quinoline-2-carboxylic acid 3.8 g (10 mmol) of the above acetyl compound were oxidized with aqueous NaOH/bromine/1,4-dioxane (haloform reaction). 3.0 g of product were obtained, melting point 117°–119° C. (from aqueous hydrochloric acid).

g) N-((3-Benzyloxy-6-(3-ethyloxy-1-propyloxy)quinolin-2-yl)carbonyl)glycine benzyl ester 2.7 g of oily product were obtained from 2.3 g (6 mmoL) of the above carboxylic acid in 300 ml of anhydrous methlene chloride with 2.0 g (6 mmol) of glycine benzyl ester tosylate, 3.3 ml (24 mmol) of NEM, 1.0 g (7.5 mmol) of HOBT and 2.7 g (6.3 mmol) of CMC analogously to Examples 4g) and 21f), after chromatography over silica gel with ethyl acetate.

h) The title compound was obtained by dissolving 2.7 g of the above dibenzyl compound in 100 ml of tetrahydrofuran and hydrogenating it with Pd/C (10%) in a duck-shaped shaking vessel. The catalyst was then filtered off with suction, the filtrate was concentrated in vacuo and the residue was crystallized with petroleum ether. 1.3 g of product were obtained, melting point 133°–135° C.

EXAMPLE 26

N-((3-Hydroxy-6-(2-propyloxy)qinolin-2-yl)carbonyl)glycine a) 2-Nitro-5-(2-propyloxy)benzyl alcohol 10 g (60 mmol) of 5-hydroxy-2-nitrobenzyl alcohol were reacted with 7.0 ml (70 mmol) of isopropyl iodide analogously to Example 4a); after purification over silica gel with n-heptane/ethyl acetate (3:2), 10.3 g of oily crude product.

b) 2-Nitro-5-(2-propyloxy)benzoic acid 10.3 g (about 50 mmol) of the above benzyl alcohol were oxidized analogously to Example 4b); 9.4 g of product, melting point 131°–133° C. (from methylene chloride).

c) 3-(5-(2-propyloxy)-2-nitrobenzoyl)acetyl acetone 12.4 g of product were obtained from 9 g (40 mmol) of the above product (analogously to Example 4c)).

d) 2-Acetyl-3-hydroxy-6-(2-propyloxy)quinoline 12.3 g (40 mmol) of the above product were reacted in 150 ml of 20% strength aqueous potassium hydroxide solution at 50° C. for 45 minutes analogously to Example 4d). Chromatography gave 4.3 g of product, melting point 95°–97° C. (from n-heptane/ethyl acetate (3:1)).

e) 2-Acetyl-3-benzyloxy-6-(2-propyloxy)quinoline 4.2 g (17 mmol) of the above substance were reacted with 1.4 g (10 mmol) of potassium carbonate and 2.9 g (2.0 ml, 17 mmol) of benzyl bromide in 100 ml of diethyl ketone, 5.0 g of product, melting point 102°–104° C. (from petroleum ether).

f) 3-Benzyloxy-6-(2-propyloxy)quinoline-2-carboxylic acid 3.4 g (10 mmol) of the above acetyl compound, dissolved in 10 ml of 1,4-dioxane, were added dropwise to a solution of 4 g of NaOH and 1.6 g (30 mmol) of bromine in 20 ml of water at 0° to 5° C. After a thick slurry had formed, 50 ml of diethyl ether were added, the mixture was stirred, 1 g of sodium disulfite in 15 ml of water was then added, the precipitate was filtered off with suction and dissolved in tetrahydrofuran/water, the solution was acidified with half-concentrated aqueous hydrochloric acid, the aqueous phase was extracted with ethyl acetate and concentrated and the residue was crystallized with diisopropyl ether. 3.0 g of product were obtained, melting point 140° C. (with decomposition). g) N-((3-Benzyloxy-6-(2-propyloxy)quinolin-2-yl)carbonyl)glycine benzyl ester 2.7 g (8 mmol) of the above quinolinecarboxylic acid were reacted with 2.7 g (8 mmol) of glycine benzyl ester tosylate, 4.4 ml (32 mmol) of NEM, 1.35 g (10 mmol) of HOBT and 3.6 g (8.8 mmol) of CMC in 300 ml of anhydrous methylene chloride at 20° C. for 24 hours, analogously to Example 25g). After working up and chromatography over silica gel with n-heptane/ethyl acetate (3:2), 3.5 g of oily product were obtained.

h) The title compound was obtained by hydrogenating 3.4 g (7 mmol) of the above dibenzyl compound in 100 ml of tetrahydrofuran with Pd/C (10%) in a duck-shaped shaking vessel (uptake of 260 ml of hydrogen). The catalyst was filtered off with suction, the filtrate was concentrated and the residue was crystallized with diisopropyl ether. 1.5 g of the colorless title compound were obtained, melting point 149°–151° C.

EXAMPLE 27

N-((3-Hydroxy-6-phenoxyquinolin-2-yl)carbonyl)glycine a) 2-Nitro-5-phenoxytoluene 14.1 g (150 mmol) of phenol were dissolved in 120 ml of anhydrous N,N-dimethylacetamide, while stirring, 20.6 g (150 mmol) of finely powdered potassium carbonate were added and the mixture was stirred at 70°–80° C. for 30 minutes. After cooling to 20° C., 23.25 g (18.3 ml, 150 mmol) of 5-fluoro-2-nitrotoluene were added dropwise, the mixture was heated at 135°–140° C. for 2 hours and, after cooling, concentrated in vacuo, the residue was introduced into ice and the crystalline product was filtered off with suction, washed with water and dried, 30 g, melting point 43°–46° C.

b) 2-Nitro-5-phenoxybenzoic acid (cf. also Liebigs Ann. 593, 113 (1955))

13 g (56.7 mmol) of the above substance were stirred under reflux with 85 g of potassium permanganate in pyridine/water (1:2) for 4 hours. The manganese dioxide was filtered off hot with suction and rinsed with hot water, the filtrate was concentrated, the residue was taken up in 250 ml of saturated aqueous Na bicarbonate solution, unreacted starting material was filtered off with suction and the filtrate was brought to pH 1 with half-concentrated HCl, 4.3 g, melting point 148°–150° C.

c) 3-(2-Nitro-5-phenoxybenzoyl)acetylacetone 12 g of oily crude product were obtained from 15.6 g (60 mmol) of the above benzoic acid with oxalyl chloride and magnesium acetylacetonide analogously to Example 4c).

d) 2-Acetyl-3-hydroxy-6-phenoxyquinoline 10 g (29.3 mmol) of the above compound were reacted in 100 ml of 20% strength aqueous KOH solution analogously to Example 4d). After chromatography of the crude product over silica gel with n-heptane/ethyl acetate (3:1), 2.5 g of product were obtained, melting point 131°–133° C. 0.55 g of the corresponding N-oxide was obtained as a byproduct, melting point 173°–175° C.

e) 2-Acetyl-3-benzyloxy-5-phenoxyquinoline 2.5 g (8.9 mmol) of the above compound were reacted with 1.2 g (8.9 mmol) of potassium carbonate and 1.1 ml (8.9 mmol) of benzyl bromide in 80 ml of diethyl ketone, 3.3 g of product, melting point 116°–118° C. (from water, sintering at 100° C.).

f) 3-Benzyloxy-6-phenoxyquinoline-2-carboxylic acid 2.2 g (5.96 mmol) of the above compound were subjected to the haloform reaction analogously to Example 4f) (12 ml of water, 2.6 g of NaOH (60 mmol), 0.9 ml (18 mmol) of bromine, 10 ml of dioxane), 2.1 g of product, melting point 281° C.–283° C.

g) N-((3-Benzyloxy-6-phenoxyquinolin-2-yl)carbonyl) glycine benzyl ester 1.5 g (4 mmol) of the above carboxylic acid were reacted with 1.35 g (4 mmol) of glycine benzyl ester tosylate, 2.2 ml (16 mmol) of NEM, 0.67 g (15 mmol) of HOBT and 1.8 g (4.2 mmol) of CMC in 250 ml of anhydrous methylene chloride analogously to Example 4g). 1.5 g of product were obtained, melting point 143°–145° C. (from diisopropyl ether).

h) The title compound was obtained by hydrogenating 1.5 g of the above glycine ester in tetrahydrofuran with Pd/C (10%) in a duck-shaped shaking vessel. 0.7 g of the title compound was obtained, melting point 225°–227° C. (from diisopropyl ether).

EXAMPLE 28

N-((3-Hydroxy -6-(3-methoxyphenoxy)quinolin-2-yl)carbonyl)glycine

The title compound was obtained analogously to Example 27.

a) 5-((3-Methoxyphenyl)oxy)-2-nitrotoluene 35 g of product were obtained from 18 g (150 mmol) of 3-methoxyphenol and 23.3 g (150 mmol) of 5-fluoro-2-nitrotoluene, melting point 48°–50° C. (from water).

b) 5-(3-Methoxyphenoxy)-2-nitrobenzoic acid Melting point 146°–151° C. (from aqueous hydrochloric acid).

c) 3-(5-((3-Methoxyphenyl)oxy)-2-nitrobenzoyl) acetylacetone
oily product after column chromatography.

d) 2-Acetyl-3-hydroxy-6-((3-methoxyphenyl)oxy) quinoline 4.9 g of product were obtained from 7.5 g (20 mmol) of the above substance after treatment with 75 ml of 20% strength KOH (90 minutes, 55° C.), melting point 102°–104° C. (from n-heptane/ethyl acetate (3:1)).

e) 2-Acetyl-3-benzyloxy-6-((3-methoxyphenyl)oxy) quinoline
oily product after chromatography over silica gel.

f) 3-Benzyloxy-6-((3-methoxyphenyl)oxy)quinoline-2-carboxylic acid,

Melting point 142° C. (with decomposition, from diisopropyl ether).

g) N-((3-Benzyloxy-6-((3-methoxyphenyl)oxy)quinolin-2-yl)carbonyl)glycine benzyl ester Melting point 118°–120° C. (from petroleum ether).

h) The title compound was obtained analogously to Example 27h).

1.1 g of product were obtained from 2 g of the above substance, melting point 166°–167° C. (from diisopropyl ether).

EXAMPLE 29

N-((3-Hydroxy-6-((3-trifluoromethylphenyl)oxy) quinolin-2-yl)carbonyl)glycine

The title compound was obtained analogously to Example 27.

a) 2-Nitro-5-((3-trifluoromethylphenyl)oxy)toluene 62 g of oily crude product were obtained from 36.5 g (225 mmol) of 3-hydroxybenzotrifluoride and 27.9 g (225 mmol) of 5-fluoro-2-nitrotoluene.

b) 2-Nitro -5-((3- trifluoromethylphenyl)oxy)benzoic acid, melting point 153°–155° C. (from aqueous hydrochloric acid).

c) 3-(2-Nitro-5-((3-trifluoromethylphenyl)oxy)benzoyl) acetylacetone 15 g of oily product were obtained from 18 g (55 mmol) of the above compound after chromatography with n-heptane/ethyl acetate (4:1).

d) 2-Acetyl-3-hydroxy-6-((3-trifluoromethylphenyl)oxy) quinoline, melting point 97°–99° C. (from petroleum ether).

e) 2-Acetyl-3-benzyloxy-6-((3-trifluoromethylphenyl) oxy)quinoline,
oily product after chromatography.

f) 3-Benzyloxy-6-((3-trifluoromethylphenyl)oxy) quinoline-2-carboxylic acid 5.7 g (13 mmol) of the above acetyl compound were oxidized analogously to Example 4f). 5.7 g of product were obtained from the organic phase without acidification, melting point 150° C. (from petroleum ether, foaming).

g) N-((3-Benzyloxy-6-((3-trifluoromethylphenyl)oxy) quinolin-2-yl)carbonyl)glycine benzyl ester 5.6 g (12.7 mmol) of the above carboxylic acid were reacted with glycine benzyl ester tosylate, NEM, HOBT and CMC analogously to Example 4g); 3.5 g of product, melting point 103°–105° C.

h) The title compound was obtained by hydrogenating 3.4 g of the above benzyl ester in tetrahydrofuran with Pd/C (10%) in a duck-shaped shaking vessel. 2.2 g of product were isolated, melting point 166°–168° C. (from petroleum ether).

EXAMPLE 30

N-((7-Chloro-3-hydroxyquinolin-2-yl)carbonyl) glycine a) 3-(4-Chloro-2-nitrobenzoyl)acetylacetone 45 g of crude product were obtained from 60.5 g (0.3 mol) of 4-chloro-2-nitrobenzoic acid analogously to Example 4e).

b) 2-Acetyl-7-chloro-3-hydroxyquinoline 18.3 g of product were obtained from 44 g (0.15 mol) of the above compound analogously to Example 4d), after chromatography over silica gel with n-heptane/ethyl acetate (2:1), melting point 97°–99° C. (from petroleum ether). 2.6 g of the corresponding N-oxide were furthermore obtained, melting point 191° C. (from diisopropyl ether).

c) 2-Acetyl-3-benzyloxy-7-chloroquinoline 7.5 g (34 mmol) of the above substance were reacted with 4.7 g (34 mmol) of potassium carbonate and 4.1 ml (34 mmol) of benzyl bromide in 120 ml of diethyl ketone. Chromatography over silica gel with n-heptane/ethyl acetate (4:1) gave 8 g of product, melting point 76°–77° C. (from petroleum ether).

d) 3-Benzyloxy-7-chloroquinoline-2-carboxylic acid 4.1 g of product were obtained from 4.7 g (15 mmol) of the above acetyl compound after haloform oxidation (NaOH/water/bromine/dioxane), melting point 140° C. (with decomposition, from water).

e) N-((3-Benzyloxy-7-chloroquinolin-2-yl)carbonyl) glycine ethyl ester 3.5 g of product were obtained from 3.2 g (10 mmol) of the above carboxylic acid, 1.4 g (10 mmol) of glycine ethyl ester hydrochloride, 3.8 ml (30 mmol) of NEM, 1.5 g (11 mmol) of HOBT and 4.3 g (10 mmol) of CMC analogously to Example 4g), melting point 138°–140° C. (from diisopropyl ether).

f) N-((3-Benzyloxy-7-chloroquinolin-2-yl)carbonyl) glycine 2.0 g (5.0 mmol) of the above glycine ethyl ester were hydrolyzed in 150 ml of 1.5N methanolic NaOH. 1.3 g of product were obtained, melting point 105°–108° C. (sintering 70° C., foaming, from diisopropyl ether).

g) The title compound was obtained by introducing 1.2 g (3.2 mmol) of the above benzyl compound into 60 ml of 48% strength aqueous hydrogen bromide and stirring the mixture at 80° C. for 45 minutes. After cooling, the mixture was concentrated in vacuo and the residue was washed three times with 50 ml of tetrahydrofuran each time to give 0.57 g of product, melting point 268°–270° C.

EXAMPLE 31

N-((7-Chloro-3-hydroxy-6-(2,2,2-trifluoroethyloxy) quinolin-2-yl)carbonyl)glycine a) 4,5-Dichloro-2-nitrotoluene 3,4-Dichlorotoluene was nitrated with concentrated sulfuric acid and fuming nitric acid (d=1.52).

b) 4-Chloro-2-nitro-5-(2,2,2-trifluoroethyloxy)toluene 40.4 g (360 mmol) of potassium tert-butylate were added in portions to 60 ml of trifluoroethanol, while stirring and cooling, and the mixture was heated to 80°–90° C. After cooling, 14.4 g (70 mmol) of 4,5-dichloro-2-nitrotoluene were added and the mixture was stirred at 105° C. for 1 hour. It was concentrated in vacuo and the residue was treated with 300 ml of water to give, after filtration with suction, 12 g of crude product, which were purified over silica gel with n-heptane/ethyl acetate, 10 g of product, melting point 76°–79° C.

c) 4-Chloro-2-nitro-5-(2,2,2-trifluoroethyloxy)benzoic acid 10 g of the above compound were oxidized in pyridine/water (1:2) with 85 g of potassium permanganate; 8.2 g of product, melting point 153°–155° C. (from aqueous hydrochloric acid).

d) 3-(4-Chloro-2-nitro-5-(2,2,2-trifluoroethyloxy) benzoyl)acetyl acetone 10.3 g of product were obtained from 10 g (34 mmol of the above acid analogously to Example 4c), melting point 138°–140° C. (from petroleum ether).

e) 2-Acetyl-7-chloro-3-hydroxy-6-(2,2,2-trifluoroethyloxy)quinoline 10.2 g (26.6 mmol) of the above compound were reacted in 100 ml of 10% strength aqueous KOH at 50°–70° C. After acidification with half-concentrated HCl, 10 g of crude product were purified over silica gel with n-heptane/ethyl acetate (4:1); 4.2 g of product, melting point 104°–105° C.

f) 2-Acetyl-3-benzyloxy-7-chloro-6-(2,2,2-trifluoroethyloxy)quinoline 4.2 g (13 mmol) of the above compound were reacted with 1.8 g (13 mmol) of potassium carbonate and 1.6 ml (13 mmol) of benzyl bromide in 100 ml of diethyl ketone, 4.4 g of product, melting point 110°–112° C. (from water).

g) Sodium 3-benzyloxy-7-chloro-6-(2,2,2-trifluoroethyloxy)quinoline-2-carboxylate 3.3 g (8 mmol) of the above acetyl compound were oxidized in aqueous NaOH/bromine/1,4-dioxane. After addition of aqueous sodium pyrosulfite ($Na_2S_2O_5$) solution, the product which had precipitated out was filtered off with suction to give 3.6 g of the sodium salt, melting point >325° C.

h) N-((3-Benzyloxy-7-chloro-6-(2,2,2-trifluoroethyloxy) quinolin-2-yl)carbonyl)glycine benzyl ester 3.3 g (8 mmol) of the above carboxylic acid were reacted with glycine benzyl ester tosylate analogously to Example 4g); 2.92 g of product, which was reacted further.

i) N-((3-Hydroxy-7-chloro-6-(2,2,2-trifluoroethyloxy) quinolin-2-yl)carbonyl)glycine-tetrahydrofuran complex (0.5 equivalent)

1.12 g (2 mmol) of the above benzyl compound were dissolved in tetrahydrofuran and hydrogenated with Pd/C (10%) in a duck-shaped shaking vessel. 0.58 g of colorless product was obtained, melting point 204°–206° C. (from petroleum ether), which, according to $^1$H-NMR, comprises 0.5 equivalent of tetrahydrofuran.

EXAMPLE 32

N-((7-Chloro-3-hydroxy-6-(2,2,3,3,3-pentafluoropropyloxy)quinolin-2-yl)carbonyl) glycine

EXAMPLE 33

N-((7-Chloro-6-(2,2,3,3,4,4,4-heptafluorobutyloxy)-3-hydroxyquinolin-2-yl)carbonyl)glycine a) 4-Chloro-4-nitro-5-(2,2,3,3,4,4,4-heptafluorobutyloxy) toluene was obtained with heptafluorobutanol analogously to Example 31b), oily crude product.

b) 4-Chloro-5-(2,2,3,3,4,4,4-heptafluorobutyloxy)-2-nitrobenzoic acid, analogously to Example 31c), melting point 115°–117° C. (from petroleum ether).

c) 3-(4-Chloro-5-(2,2,3,3,4,4,4-heptafluorobutyloxy)-2-nitrobenzoyl)acetylacetone 7.77 g of product were obtained from 7.7 g (19 mmol) of the above acid analogously to Examples 31d) and 4c), melting point 80°–81° C. (from petroleum ether).

d) 2-Acetyl-7-chloro-6-(2,2,3,3,4,4,4-heptafluorobutyloxy)-3-hydroxyquinoline was obtained from 7.7 g of the above compound analogously to Example 31e), 2.9 g of oily product after chromatography over silica gel with n-heptane/ethyl acetate (4:1).

e) 2-Acetyl-3-benzyloxy-7-chloro-6-(2,2,3,3,4,4,4-heptafluorobutyloxy)quinoline 3.8 g of oily product were obtained from 2.9 g (6.9 mmol) of the above compound analogously to Example 31f).

f) 3-Benzyloxy-7-chloro-6-(2,2,3,3,4,4,4-heptafluorobutyloxy)quinoline-2-carboxylic acid 3.4 g of product were obtained from 3.6 g (7 mmol) of the above acetyl compound analogously to Example 31g), melting point 183°–185° C. (from petroleum ether).

g) N-((3-Benzyloxy-7-chloro-6-(2,2,3,3,4,4,4-heptafluorobutyloxy)quinolin-2-yl)carbonyl)glycine benzyl ester h) 3.3 g (6.5 mmol) of the above carboxylic acid were reacted with glycine benzyl ester tosylate analogously to Example 4g). After purification of the crude product over silica gel with n-heptane/ethyl acetate (2:1), 3.3 g of oily product were obtained.

i) 1.32 g (2 mmol) of the above compound were hydrogenated analogously to Example 31i); 0.72 g of colorless product, melting point 172°–173° C. (from petroleum ether).

EXAMPLE 34

N-((3-Hydroxy-6-(2-propyl)quinolin-2-yl)carbonyl)glycine

EXAMPLE 35

N-((3-Hydroxy-5-phenoxyquinolin-2-yl)carbonyl)glycine

EXAMPLE 36

N-((5-(1,3-Dichlorophenoxy)-3-hydroxyquinolin-2-yl)carbonyl)glycine

EXAMPLE 37

N-((5-(1-Butyloxy)-3-hydroxyquinolin-2-yl)carbonyl)glycine

EXAMPLE 38

N-((6-(1-Butyl)-3-hydroxyquinolin-2-yl)carbonyl)glycine

EXAMPLE 39

N-((6-(1-Hexyl)-3-hydroxyquinolin-2-yl)carbonyl)glycine

EXAMPLE 40

N-((6-(1-Decyl)-3-hydroxyquinolin-2-yl)carbonyl)glycine

EXAMPLE 41

N-((3-Hydroxy-6-(1-octyl)quinolin-2-yl)carbonyl)glycine

EXAMPLE 42

N-((3-Hydroxy-6-phenylquinolin-2-yl)carbonyl)glycine

EXAMPLE 43

N-((3-Hydroxy-6-(2,2,3,3-tetrafluoropropyloxy)quinolin-2-yl)carbonyl)glycine a) 2-Nitro-5-(2,2,3,3-tetrafluoropropyloxy)toluene 28 g of potassium carbonate, 70 ml of tetrafluoropropanol and 26.4 g of 5-fluoro-2-nitrotoluene were reacted; 45 g of oily crude product.

b) 2-Nitro-5-(2,2,3,3-tetrafluoropropyloxy)benzoic acid,

Melting point 140° C. (with foaming, from aqueous hydrochloric acid).

c) 3-(2-Nitro-5-(2,2,3,3-tetrafluoropropyloxy)benzoyl)acetylacetone, oily product.

d) 2-Acetyl-3-hydroxy-6-(2,2,3,3-tetrafluoropropyloxy)quinoline 13.3 g (35 mmol) of the above substance were stirred in 125 ml of 20% strength aqueous KOH at 50° C. for 45 minutes; 7.5 g of product, melting point 119°–121° C. (from petroleum ether).

e) 2-Acetyl-3-benzyloxy-6-(2,2,3,3-tetrafluoropropyloxy)quinoline

Melting point 121°–123° C. (from petroleum ether).

f) 3-Benzyloxy-6-(2,2,3,3-tetrafluoropropyloxy)quinoline-2-carboxylic acid

Melting point 123° C. (with decomposition, from petroleum ether).

g) N-((3-Benzyloxy-6-(2,2,3,3-tetrafluoropropyloxy)quinolin-2-yl)carbonyl)glycine benzyl ester, melting point 99°–101° C. (from petroleum ether).

h) The title compound was obtained by hydrogenation of the above benzyl compound, melting point 175°–177° C. (from petroleum ether).

EXAMPLE 44

N-((3-Hydroxy-6-(2,2,3,3,4,4,5,5-octafluoropentyloxy)quinolin-2-yl)carbonyl)glycine a) 2-Nitro-5-(2,2,3,3,4,4,5,5-octafluoropentyloxy)toluene prepared from 5-fluoro-2-nitrotoluene and octafluoro-1-pentanol, oil.

b) 2-Nitro-5-(2,2,3,3,4,4,5,5-octafluoropentyloxy)benzoic acid

Melting point 95°–96° C. (from petroleum ether).

c) 3-(2-Nitro-5-(2,2,3,3,4,4,5,5-octafluoropentyloxy)benzoyl)acetylacetone oily product.

d) 2-Acetyl-3-hydroxy-6-(2,2,3,3,4,4,5,5-octafluoropentyloxy)quinoline

Melting point 69°–71° C. (from n-heptane/ethyl acetate (3:1)).

e) 2-Acetyl-3-benzyloxy-6-(2,2,3,3,4,4,5,5-octafluoropentyloxy)quinoline f) 3-Benzyloxy-6-(2,2,3,3,4,4,5,5-octafluoropentyloxy)quinoline-2-carboxylic acid, resinous product.

g) N-((3-Benzyloxy-(2,2,3,3,4,4,5,5-octafluoropentyloxy)quinolin-2-yl)carbonyl)-glycine benzyl ester, oil.

h) The title compound was obtained by hydrogenation, melting point 170°–172° C. (sintering 115° C., from petroleum ether).

EXAMPLE 45
N-((6-((3-Chlorophenyl)oxy)-3-hydroxyquinolin-2-yl)carbonyl)glycine

EXAMPLE 46
N-((6-((3-Fluorophenyl)oxy)-3-hydroxyquinolin-2-yl)carbonyl)glycine

EXAMPLE 47
N-((3-Hydroxy-6-(3-(1-propyloxy)phenyloxy)quinolin-2-yl)carbonyl)glycine EXAMPLE 48
N-((6-(3-((Cyclohexylamino)carbonyl)phenyloxy)-3-hydroxyquinolin-2-yl)carbonyl)glycine EXAMPLE 49
N-((6-((4-Chlorophenyl)sulfonyl)-3-hydroxyquinolin-2-yl)carbonyl)glycine EXAMPLE 50
N-((3-Hydroxy-6-((4-(2,2,2-trifluoroethyloxy)phenyl)sulfonyl)quinolin-2-yl)carbonyl)glycine EXAMPLE 51
N-((3-Hydroxy-6-((4-methoxyphenyl)sulfonyl)quinolin-2-yl)carbonyl)glycine EXAMPLE 52
N-((3-Hydroxy-6-((4-(1-propyloxy)phenyl)sulfonyl)quinolin-2-ylcarbonyl)glycine EXAMPLE 53
N-((6-((4-(1-Butyloxy)phenyl)sulfonyl)-3-hydroxyquinolin-2-yl)carbonyl)glycine EXAMPLE 54
N-((6-((3-Chlorophenyl)sulfonyl)-3-hydroxyquinolin-2-yl)carbonyl)glycine EXAMPLE 55
N-((3-Hydroxy-6-((3-methoxyphenyl)sulfonyl)quinolin-2-yl)carbonyl)glycine EXAMPLE 56
N-((3-Hydroxy-6-((3-trifluoromethylphenyl)sulfonyl)quinolin-2-yl)carbonyl)glycine EXAMPLE 57
N-((6-((4-Ethyloxyphenyl)sulfonyl)-3-hydroxyquinolin-2-yl)carbonyl)glycine EXAMPLE 58
N-((6-((4-Bromophenyl)sulfonyl)-3-hydroxyquinolin-2-yl)carbonyl)glycine EXAMPLE 59
N-((6-((4-(3-Ethyloxypropyloxy)phenyl)sulfonyl)-3-hydroxyquinolin-2-yl)carbonyl)glycine EXAMPLE 60
N-((6-((2,5-Dichlorophenyl)sulfonyl)-3-hydroxyquinolin-2-yl)carbonyl)glycine EXAMPLE 61
N-((6-((3,4-Dichlorophenyl)sulfonyl)-3-hydroxyquinolin-2-yl)carbonyl)glycine EXAMPLE 62
N-((6-((3,5-Dichlorophenyl)sulfonyl)-3-hydroxyquinolin-2-yl)carbonyl)glycine EXAMPLE 63
N-((6-((3,4-Dimethoxyphenyl)sulfonyl)-3-hydroxyquinolin-2-yl)carbonyl)glycine EXAMPLE 64
N-((6-((3,5-Bis-trifluoromethylphenyl)sulfonyl)-3-hydroxyquinolin-2-yl)carbonyl)glycine EXAMPLE 65
N-((3-Hydroxy-6-((4-trifluoromethoxyphenyl)sulfonyl)quinolin-2-yl)carbonyl)glycine EXAMPLE 66
N-((3-Hydroxy-6-((4-trifluoromethylphenyl)sulfonyl)quinolin-2-yl)carbonyl)glycine EXAMPLE 67
N-((3-Hydroxy-6-((4-(1-propyl)phenyl)sulfonyl)quinolin-2-yl)carbonyl)glycine EXAMPLE 68
N-((-6-((4-(1-Butyl)phenyl)sulfonyl)-3-hydroxyquinolin-2-yl)carbonyl)glycine EXAMPLE 69
N-((3-Hydroxy-6-(1-naphthylsulfonyl)quinolin-2-yl)carbonyl)glycine EXAMPLE 70
N-((3-Hydroxy-6-(2-naphthylsulfonyl)quinolin-2-yl)carbonyl)glycine

What is claimed is:
1. A compound of the formula II

$$\begin{array}{c} R^2 \quad R^1 \\ R^3 \underset{R^4}{\underset{R^5}{\diagdown}} \diagup OR^{10} \\ \diagdown N \diagup CO_2R^{11} \end{array} \quad (II)$$

in which $R^1$, $R^2$, $R^3$, $R^4$ and $R^5$ are identical or different and are hydrogen, hydroxyl, halogen, cyano, trifluoromethyl, nitro, carboxyl, $(C_1–C_{20})$-alkyl, $(C_3–C_8)$-cycloalkyl, $(C_3–C_8)$-cycloalkyl-$(C_1–C_{12})$-alkyl, $(C_3–C_8)$-cycloalkoxy, $(C_3–C_8)$-cycloalkyl-$(C_1–C_{12})$-alkoxy, $(C_3–C_8)$-cycloalkyloxy-$(C_1–C_{12})$-alkyl, $(C_3–C_8)$-cycloalkyloxy-$(C_1–C_{12})$-alkoxy, $(C_3–C_8)$-cycloalkyl-$(C_1–C_{12})$-alkyl-$(C_1–C_6)$-alkoxy, $(C_3–C_8)$-cycloalkyl-$(C_1–C_8)$-alkoxy-$(C_3–C_8)$-alkyl, $(C_3–C_8)$-cycloalkyloxy-$(C_1–C_8)$-alkoxy-$(C_1–C_6)$-alkyl, $(C_3–C_8)$-cycloalkoxy-$(C_1–C_8)$-alkoxy-$(C_1–C_8)$-alkoxy, $(C_6–C_{12})$-aryl, $(C_7–C_{16})$-aralkyl, $(C_7–C_{16})$-aralkenyl, $(C_7–C_{16})$-aralkynyl, $(C_2–C_{20})$-alkenyl, $(C_2–C_{20})$-alkynyl, $(C_1–C_{20})$-alkoxy, $(C_2–C_{20})$-alkenyloxy, $(C_2–C_{20})$-alkynyloxy, retinyloxy, $(C_1–C_{20})$-alkoxy-$(C_1–C_{12})$-alkyl, $(C_1–C_{12})$-alkoxy-$(C_1–C_{12})$-alkoxy, $(C_1–C_{12})$-alkoxy-$(C_1–C_{12})$-alkoxy-$(C_1–C_8)$-alkyl, $(C_6–C_{12})$-aryloxy, $(C_7–C_{16})$-aralkyloxy, $(C_6–C_{12})$-aryloxy-$(C_1–C_6)$-alkoxy, $(C_7–C_{16})$-araloxy-$(C_1–C_6)$-alkoxy, $(C_1–C_{16})$-hydroxyalkyl, $(C_6–C_{16})$-aryloxy-$(C_1–C_8)$-alkyl, $(C_7–C_{16})$-aralkoxy-$(C_1–C_8)$-alkyl, $(C_6–C_{12})$-aryloxy-$(C_1–C_8)$-alkoxy-$(C_1–C_6)$-alkyl, $(C_7–C_{12})$-aralkyloxy-$(C_1–C_8)$-alkoxy-$(C_1–C_6)$-alkyl, $(C_2–C_{20})$-alkenyloxy-$(C_1–C_8)$-alkyl, $(C_2–C_{20})$-alkynyloxy-$(C_1–C_8)$-alkyl, retinyloxy-$(C_1–C_6)$-alkyl, $—O—CH_{2l-]_x}C_fH_{(2f+1-g)}Hal_g$, $(C_1–C_6)$-chlorofluoroalkoxy, $(C_1–C_{20})$-alkylcarbonyl, $(C_3–C_8)$-cycloalkylcarbonyl, $(C_6–C_{12})$-arylcarbonyl, $(C_7–C_{16})$-aralkylcarbonyl, cinnamoyl, $(C_2–C_{20})$-alkenylcarbonyl, $(C_2–C_{20})$-alkynylcarbonyl, $(C_1–C_{20})$-alkoxycarbonyl, $(C_1–C_{12})$-alkoxy-$(C_1–C_{12})$-alkoxycarbonyl, $(C_6–C_{12})$-aryloxycarbonyl, $(C_7–C_{16})$-aralkoxycarbonyl, $(C_3–C_8)$- cycloalkoxycarbonyl, $(C_2-C_{20})$-alkenyloxycarbonyl, retinyloxycarbonyl, $(C_2-C_{20})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy,
$(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy,
carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-$((C_3-C_8)$-cycloalkyl-$(C_1-C_6)$-alkyl)carbamoyl, N-$(C_1-C_6)$-alkyl-N-$((C_3-C_8)$-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{12})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{12})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl) carbamoyl, $CON(CH_2)_h$, in which a $CH_2$ group can be replaced by O, S, N-$(C_1-C_{12})$-alkylimino, N-$(C_3-C_8)$-cycloalkylimino, N-$(C_3-C_8)$-cycloalkyl-$(C_1-C_{12})$-alkylimino, N-$(C_6-C_{12})$-arylimino, N-$(C_7-C_{16})$-aralkylimino or N-$(C_1-C_{12})$-alkoxy-$(C_1-C_6)$-alkylimino, or a carbamoyl radical of the formula J

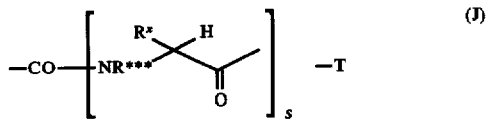
(J)

in which
$R^x$ is the substituent of an L- or D-α-amino acid,
S is 1, 2, 3, 4 or 5 and
T is OH, OR or NR*R**, in which
R*, R and R* are identical or different and are hydrogen, $(C_6-C_{12})$-aryl, $(C_7-C_{11})$-aralkyl, $(C_1-C_8)$-alkyl, $(C_3-C_8)$-cycloalkyl, (+)-dehydroabietyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkylcarbonyl, optionally substituted $(C_7-C_{16})$-aralkylcarbonyl or optionally substituted $(C_6-C_{12})$-arylcarbonyl, or
R* and R** together are —$[CH_2]_h$, in which one $CH_2$ group can be replaced by O, S, SO, $SO_2$, N-acylamino, N-$(C_1-C_{10})$-alkoxycarbonylimino, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, or further wherein $R^1$, $R^2$, $R^3$, $R^4$ and $R^5$ are identical or different and are:

carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{12})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkyl)carbamoyloxy, N-$((C_6-C_{12})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy)-$(C_1-C_{10})$-alkyl)carbamoyloxy, N-$(C_1-C_{10})$-alkyl-N-$((C_6-C_{12})$-aryloxy)-$(C_1-C_{10})$-alkyl)carbamoyloxy, N-$(C_1-C_{10})$-alkyl-N-$((C_7-C_{16})$-aralkyloxy-$(C_1-C_{10})$-alkyl) carbamoyloxy, $NR^yR^z$, wherein $R^y$ and $R^z$ are independently selected from $(C_1-C_{12})$-alkyl, $(C_3-C_{12})$-alkenyl, $(C_3-C_{12})$-alkynyl, $(C_6-C_{12})$-aryl, $(C_7-C_{11})$-aralkyl, $(C_1-C_{12})$-alkoxy, $(C_7-C_{12})$-aralkoxy,
$(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, and further wherein $R^y$ and $R^z$ together are —$[CH_2]_h$—, wherein one CH group can be replaced by O, S, N-$(C_1-C_4)$-alkylcarbonylimino or N-$(C_1-C_4)$-alkoxycarbonylimino, $(C_1-C_{12})$-alkylcarbonylamino-$(C_1-C_8)$-alkyl, $(C_3-C_8)$-cycloalkylcarbonylamino-$(C_1-C_8)$-alkyl, $(C_6-C_{12})$-arylcarbonylamino-$(C_1-C_8)$-alkyl, $(C_7-C_{16})$-aralkylcarbonylamino-$(C_1-C_8)$-alkyl, amino-$(C_1-C_{10})$-alkyl, N-$(C_1-C_{10})$-alkylamino-$(C_1-C_{10})$-alkyl, N,N-di $(C_1-C_{10})$-alkyl-amino-$(C_1-C_{10})$-alkyl, $(C_3-C_8)$-cycloalkylamino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, $(C_1-C_{12})$-alkylmercapto-$(C_1-C_6)$-alkyl, $(C_1-C_{12})$-alkylsulfinyl-$(C_1-C_6)$-alkyl, $(C_1-C_{12})$-alkylsulfonyl-$(C_1-C_6)$-alkyl, $(C_6-C_{12})$-arylmercapto-$(C_1-C_6)$-alkyl, $(C_6-C_{12})$-arylsulfinyl-$(C_1-C_6)$-alkyl, $(C_6-C_{12})$-arylsulfonyl-$(C_1-C_6)$-alkyl, $(C_7-C_{16})$-aralkylmercapto-$(C_1-C_6)$-alkyl, $(C_7-C_{16})$-aralkylsulfinyl-$(C_1-C_6)$-alkyl, $(C_7-C_{16})$-aralkylsulfonyl-$(C_1-C_6)$-alkyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{12})$-arylsulfamoyl, N-$(C_7-C_{16})$-aralkylsulfamoyl, N-$(C_1-C_{10})$-alkyl-N-$(C_6-C_{12})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$-alkyl)-$(C_1-C_{10})$-alkylsulfonamido, $(C_7-C_{16})$-aralkylsulfonamido, or N-$(C_1-C_{10})$-alkyl-$(C_7-C_{16})$-alkylsulfonamido, where the radicals which contain an aryl radical can in turn be substituted on the aryl by 1 to 5 identical or different radicals from the series comprising:

hydroxyl, halogen, cyano, trifluoromethyl, nitro, carboxyl, $(C_1-C_{16})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_8)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, —O—[$CH_2$]$_x C_y H_{(2y+1-g)} F_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$ aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-(($C_3-C_8$)-cycloalkyl-$(C_1-C_6)$-alkyl)carbamoyl, N-$(C_1-C_6)$-alkyl-N-(($C_3-C_8$)-cycloalkyl-$(C_1-C_8)$-alkyl)carbamoyl, N-(+)-dehydroabietylcarbamoyl, N-$(C_1-C_8)$-alkyl-N-(+)-dehydroabietylcarbamoyl, N-$(C_6-C_{12})$-arylcarbamoyl, N-$(C_7-C_{16})$-aralkyl-carbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-(($C_1-C_{16}$)-alkoxy-$(C_1-C_{10})$-alkyl)carbamoyl, N-(($C_6-C_{16}$)-aryloxy-$(C_1-C_{10})$-alkyl)carbamoyl, N-(($C_7-C_{16}$)-aralkyloxy-$(C_1-C_{10})$-alkyl)carbamoyl, N-$(C_1-C_{10})$-alkyl-N-(($C_1-C_{10}$)-alkoxy-$(C_1-C_{10})$-alkyl)carbamoyl, N-$(C_1-C_{10})$-alkyl-N-(($C_6-C_{12}$)-aryloxy-$(C_1-C_{10})$-alkyl)carbamoyl, N-$(C_1-C_{10})$-alkyl-N-(($C_7-C_{16}$)-aralkyloxy-$(C_1-C_{10})$-alkyl)carbamoyl, CON(CH$_2$)$_h$, in which one CH$_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-(($C_1-C_{10}$)-alkyl)carbamoyloxy, N-(($C_6-C_{12}$)-aryloxy-$(C_1-C_{10})$-alkyl)carbamoyloxy, N-(($C_7-C_{16}$)-aralkyloxy-$(C_1-C_{10})$-alkyl)carbamoyloxy, N-$(C_1-C_{10})$-alkyl-N-(($C_1-C_{10}$)-alkoxy-$(C_1-C_{10})$-alkyl)carbamoyloxy, N-$(C_1-C_{10})$-alkyl-N-(($C_6-C_{12}$)-aryloxy-$(C_1-C_{10})$-alkyl)

carbamoyloxy, N-$(C_1-C_{10})$-alkyl-N-(($C_7-C_{16}$)-aralkyloxy-$(C_1-C_{10})$-alkyl)-carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkylcarbonylamino, $(C_3-C_8)$-cycloalkylcarbonylamino, $(C_6-C_{12})$-arylcarbonylamino, $(C_7-C_{16})$-aralkylcarbonylamino, $(C_1-C_{12})$-alkylcarbonyl-N-$(C_1-C_{10})$-alkylamino, $(C_3-C_8)$-cycloalkylcarbonyl-N-$(C_1-C_{10})$-alkylamino, $(C_6-C_{12})$-arylcarbonyl-N-$(C_1-C_{10})$-alkylamino, $(C_7-C_{11})$-aralkylcarbonyl-N-$(C_1-C_{10})$-alkylamino, $(C_1-C_{12})$-alkylcarbonylamino-$(C_1-C_8)$-alkyl, $(C_3-C_8)$-cyclo-alkylcarbonylamino-$(C_1-C_8)$-alkyl, $(C_6-C_{12})$-arylcarbonylamino-$(C_1-C_8)$-alkyl, $(C_7-C_{16})$-aralkylcarbonylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl and $(C_7-C_{16})$-aralkylsulfonyl, sulfamoyl, N-$(C_1-C_4)$-sulfamoyl, N,N-di-$(C_1-C_4)$-sulfamoyl, or optionally carries up to 3 of said radical substituents for said aryl and further wherein two adjacent carbon atoms of an arylalkoxy radical recited in the definition of $R^1$–$R^5$ together carry a chain —[CH$_2$]— and/or —CH=CH—CH=CH—, where one CH$_2$ group of the chain is optionally replaced by O, S, SO, SO$_2$, or NR'; or $R^1$ and $R^2$, $R^2$ and $R^3$, $R^3$ and $R^4$, or $R^4$ and $R^5$ form a chain [CH$_2$]$_o$, in which one or two CH$_2$ groups of the chain, which is saturated or unsaturated with a C=C double bond, are optionally replaced by O, S, SO, SO$_2$ or NR', in which O is 3, 4 or 5, and R' is hydrogen, $(C_6-C_{12})$-aryl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, and f is 1 to 8, g is 0 or 1 to (2f+1), x is 0 to 3 and h is 3 to 6

$R^{10}$ is hydrogen or an HO-protecting group and $R^{11}$ is hydrogen, $(C_1-C_8)$-alkyl or benzyl, with the exception of compounds of the formula II in which $R^{10}$ is benzyl or methyl if $R^1$ to $R^5$ are hydrogen and $R^{11}$ is hydrogen; those compounds of the formula II in which $R^{10}$ is methyl if $R^1$ to $R^5$ are hydrogen and $R^{11}$ is methyl; those compounds of the formula II in which $R^{10}$ is hydrogen, benzyl or p-toluenesulfonyl if $R^1$ to $R^5$ are hydrogen and $R^{11}$ is ethyl; those compounds of formula II in which $R^3$ is hydrogen or methoxy if $R^1$, $R^2$, $R^4$, $R^5$, $R^{10}$ and $R^{11}$ are hydrogen, and those compounds of formula II in which $R^1$ is hydroxy or methyl and $R^2$ to $R^5$, $R^{10}$ and $R^{11}$ are hydrogen or a physiologically active salt thereof.

* * * * *

UNITED STATES PATENT AND TRADEMARK OFFICE
CERTIFICATE OF CORRECTION

PATENT NO. : 5,726,305
DATED : March 10, 1998
INVENTOR(S) : Klaus Weidmann et al.

It is certified that error appears in the above-identified patent and that said Letters Patent is hereby corrected as shown below:

Column 38,
Line 43, change "$(C_3-C_8)$-alkyl" to -- $(C_1-C_6)$-alkyl --;
Line 60, change "$CH_{2]}$-" to -- $[CH_{2\text{-}}]$ --;

Column 39,
Line 5, change "$(C_1-C_{6\text{-}})$" to -- $(C,-C_6)$ --;
Line 6, change "$(C_3-C_8\text{-}$" to -- $(C_3-C_8)$ --;

Column 40,
Line 53, change "alkylsulfonamido" to -- alkysulfonamido --;

Signed and Sealed this

Ninth Day of July, 2002

Attest:

JAMES E. ROGAN
Attesting Officer      Director of the United States Patent and Trademark Office